United States Patent
Subramanian

(12) 
(10) Patent No.: US 6,500,639 B2
(45) Date of Patent: *Dec. 31, 2002

(54) DNA SHUFFLING TO PRODUCE NUCLEIC ACIDS FOR MYCOTOXIN DETOXIFICATION

(75) Inventor: Venkiteswaran Subramanian, San Diego, CA (US)

(73) Assignee: Maxygen, Inc., Redwood City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/414,084

(22) Filed: Oct. 6, 1999

(65) Prior Publication Data

US 2002/0184661 A1 Dec. 5, 2002

Related U.S. Application Data

(60) Provisional application No. 60/103,441, filed on Oct. 7, 1998.

(51) Int. Cl.[7] ............ C12P 21/06; C12N 15/63; C12N 15/82; C12N 15/79; C12N 15/85
(52) U.S. Cl. ............ 435/69.1; 435/455; 435/468; 435/471; 435/DIG. 5; 435/DIG. 47; 800/279
(58) Field of Search ............ 435/471, 6, 172, 435/69.1, 455, 468, DIG. 5, DIG. 47; 800/279

(56) References Cited

U.S. PATENT DOCUMENTS

| | | |
|---|---|---|
| 5,512,463 | 4/1996 | Stemmer |
| 5,514,588 | 5/1996 | Varadaraj |
| 5,521,077 | 5/1996 | Khosla et al. |
| 5,605,793 | 2/1997 | Stemmer |
| 5,763,239 | 6/1998 | Short et al. |
| 5,789,228 | 8/1998 | Lam et al. |
| 5,792,931 * | 8/1998 | Duvick et al. ............ 800/205 |
| 5,811,238 | 9/1998 | Stemmer et al. |
| 5,814,473 | 9/1998 | Warren et al. |
| 5,824,469 | 10/1998 | Horwitz et al. |
| 5,830,696 | 11/1998 | Short |
| 5,830,721 | 11/1998 | Stemmer et al. |
| 5,834,252 | 11/1998 | Stemmer et al. |
| 5,837,458 * | 11/1998 | Minshull et al. ............ 435/6 |
| 5,866,363 | 2/1999 | Pieczenik |
| 5,876,997 | 3/1999 | Kretz |
| 5,925,749 | 7/1999 | Mathur et al. |
| 5,928,905 | 7/1999 | Stemmer et al. |
| 5,939,250 | 8/1999 | Short |
| 5,939,300 | 8/1999 | Robertson et al. |
| 5,942,430 | 8/1999 | Robetson et al. |
| 5,948,666 | 9/1999 | Callen et al. |
| 5,958,672 | 9/1999 | Short |
| 5,958,751 | 9/1999 | Murphy et al. |
| 5,962,258 | 10/1999 | Mathur et al. |
| 5,962,283 | 10/1999 | Warren et al. |
| 5,965,408 | 10/1999 | Short |
| 5,985,646 | 11/1999 | Murphy et al. |
| 6,001,574 | 12/1999 | Short et al. |
| 6,004,788 | 12/1999 | Short |
| 6,030,779 | 2/2000 | Short |
| 6,054,267 | 4/2000 | Short |
| 6,096,548 | 8/2000 | Stemmer |
| 6,117,679 | 9/2000 | Stemmer |
| 6,132,970 | 10/2000 | Stemmer |

FOREIGN PATENT DOCUMENTS

| | | |
|---|---|---|
| EP | 0911396 A2 | 4/1999 |
| EP | 0911396 A3 | 5/1999 |
| EP | 0934999 A1 | 8/1999 |
| WO | WO93/22443 | 11/1993 |
| WO | WO95/22625 | 8/1995 |
| WO | WO 96/06175 A2 | 2/1996 |
| WO | WO 96/12414 A1 | 5/1996 |
| WO | WO97/07205 | 2/1997 |
| WO | WO97/20078 | 6/1997 |
| WO | WO 97/20078 A1 | 6/1997 |
| WO | WO97/25410 | 7/1997 |
| WO | WO97/35957 | 10/1997 |
| WO | WO 97/35966 A1 | 10/1997 |
| WO | WO97/35966 | 10/1997 |
| WO | WO97/44361 | 11/1997 |
| WO | WO97/48416 | 12/1997 |
| WO | WO97/48717 | 12/1997 |
| WO | WO97/48794 | 12/1997 |
| WO | WO98/00526 | 1/1998 |
| WO | WO98/01581 | 1/1998 |
| WO | WO98/13487 | 4/1998 |
| WO | WO98/163485 | 4/1998 |
| WO | WO 98/23758 A1 | 6/1998 |
| WO | WO98/24799 | 6/1998 |
| WO | WO98/27230 | 6/1998 |
| WO | WO 98/27230 A1 | 6/1998 |
| WO | WO98/28416 | 7/1998 |
| WO | WO 98/31816 A1 | 7/1998 |

(List continued on next page.)

OTHER PUBLICATIONS

Goodman and Gilman's "The Pharmacological Basis of Therapeutics," 9th edition, McGraw–Hill Publishing (1996) pp. 12–16.*
Hara and Hutchinson (1992) *J. Bacteriol.* 174:5141–5144.
Kowalczkowski & Zarling *Gene Targeting* (CRC 1995), Ch. 7.
Sung (1997) *Genes Dev.* 11:1111–1121.
Sena & Zarling, *Nature Genetics* 3, 265 (1996).
Chang, C., et al. (1999) "Evolution of a cytokine using DNA family shuffling." *Nature Biotechnology* 17:793–797.
Christians, F.C. et al., (1999) "Directed evolution of thymidine kinase for AZT phosphorylation using DNA family shuffling." *Nature Biotechnology* 17:259–264.

(List continued on next page.)

*Primary Examiner*—Jyothsna Venkat
*Assistant Examiner*—Thomas Friend
(74) *Attorney, Agent, or Firm*—Norman J. Kruse; Christopher M. Holman

(57) ABSTRACT

Methods of shuffling nucleic acids to acquire or enhance mycotoxin detoxification activity, libraries of shuffled mycotoxin detoxification nucleic acids, transgenic cells, plants and DNA shuffling mixtures are provided.

21 Claims, No Drawings

FOREIGN PATENT DOCUMENTS

| WO | WO98/31837 | 7/1998 |
|---|---|---|
| WO | WO 98/31837 A1 | 7/1998 |
| WO | WO98/36080 | 8/1998 |
| WO | WO98/41622 | 9/1998 |
| WO | WO98/41623 | 9/1998 |
| WO | WO98/41653 | 9/1998 |
| WO | WO98/42832 | 10/1998 |
| WO | WO98/48034 | 10/1998 |
| WO | WO98/58085 | 12/1998 |
| WO | WO99/07837 | 2/1999 |
| WO | WO99/08539 | 2/1999 |
| WO | WO99/10472 | 3/1999 |
| WO | WO99/10539 | 3/1999 |
| WO | WO99/19518 | 4/1999 |
| WO | WO99/21979 | 5/1999 |
| WO | WO99/23107 | 5/1999 |
| WO | WO99/23236 | 5/1999 |
| WO | WO99/41368 | 8/1999 |
| WO | WO99/41369 | 8/1999 |
| WO | WO99/41383 | 8/1999 |
| WO | WO99/41402 | 8/1999 |
| WO | WO99/45154 | 9/1999 |
| WO | WO99/57128 | 11/1999 |
| WO | WO99/65927 | 12/1999 |
| WO | WO 00/04158 A2 | 1/2000 |
| WO | WO 00/04160 A1 | 1/2000 |
| WO | WO00/42560 | 7/2000 |
| WO | WO00/42561 | 7/2000 |
| WO | WO00/53744 | 9/2000 |
| WO | WO00/58517 | 10/2000 |
| WO | WO01/05980 | 1/2001 |

OTHER PUBLICATIONS

Crameri et al., (1993) "10(20)–Fold aptamer library amplification without gel purification," *Nuc. Acids. Res.* 21(18):4410.

Crameri, A. & Stemmer W.P.C. (1995) "Combinatorial multiple cassette mutagenesis creates all the permutations of mutant and wildtype cassettes." *Biotechiques* 18:194–195.

Gates, C.M. et al., (1996) "Affinity selective isolation of ligands from peptide libraries through display on a lac repressor headpiece dimer". *Journal of Molecular Biology* 255:373–386.

Minshull, J., Stemmer, W.P.C. (1999) "Protein evolution by molecular breeding." *Current Opinion in Chemical Biology* 3:284–290.

Ness, J. et al., (1999) "DNA shuffling of subgenominc sequences of subtilisin." *Nature Biotechnology* 17:893–896.

Patten, P.A. et al., (1997) "Application of DNA Shuffling to Pharmaceuticals and Vaccines." *Current Opinion in Biotechnology* 8:724–733.

Stemmer, W.P.C. (1996) "Sexual PCR and Assembly PCR." In: *The Encyclopedia of Molecular Biology*. VCH Publishers, New York. pp. 447–457.

Stemmer, W.P.C. & Soong, N.W. (1999) "Molecular breeding of viruses for targeting and other clinical properties." *Tumor Targeting* 4:59–62.

Zhang, J. et al., (1997) "Directed evolution of an effective fucosidase from a galactosidase by DNA shuffling and screening." *Proceedings of the National Academy of Sciences, USA* 94:4504–4509.

Brown et al., (1996) *PNAS* 93:1418–1422.

Clever (1997) *EMBO J.* 16:2535–2544.

Durrenberger et al., *Proc. Natl. Acad. Sci. USA* 86:9154–9158 (1996).

Feng and Leonard *Journal of Bacteriology* 177(21):6264–6254.

Kelkar et al., (1997) *JCB* 1589–1594.

Kiianitsa (1997) *Proc. Natl. Sci. USA* 94:7837–7840.

Kimura et al., (1997) *JCB* 273(3):1654–1661.

Namsaraev (1997) *Mol. Cell. Biol.* 17:5359–5368.

Revet et al., *J. Mol. Biol.* 232, 779–791 (1993).

Silva (1996) *JBC* 271(23):113600–13608.

Wold (1997) *Annu. Rev. Biochem.* 66:61–92.

Yu and Leonard (1995) *Journal of Bacteriology* 177(16):4792–4800.

Cline (1996) *Nucleic Acids Res.* 24:3546–3551.

Crameri et al., 1996. "Improved Green Fluorescent Protein by Molecular Evolution Using DNA Shuffling." *Nature Biotechnology*. vol. 14: pp. 315–319.

Cramer et al., *Nature Medicine* 2(1):1–3 (1996).

Jung (1992) *Gene* 121:17–24.

Levichkin (1995) *Mol. Biology* 29:572–577.

May et al., *J. Biol. Chem.* 248:1725–1730.

May *J. Am. Chem. Soc..*, 98:7856–7858.

Stemmer et al., 1995. "Single–step assembly of a gene and entire plasmid from large numbers of oligodeoxynucleotides." vol. 164: pp. 49–53.

Stemmer, 1994 "DNA shuffling by random fragmentation and reassembly: In vitro recombination for moelcular evolution." *Proc. Natl. Acad. Sci. USA*. vol. 91: pp. 10747–10751.

Stemmer, 1994. "Rapid evolution of a protein in vitro by DNA shuffling." Nature. vol. 370 No. 4: pp. 389–391.

Stemmer, 1995. "Searching Sequence Space." *Bio/Technology*. vol. 13: pp. 549–553.

Stemmer, 1995. "The Evolution of Molecular Computation." vol. 270: p. 1510.

Wang (1997) *biochemistry* 36:9486–9492.

Crameri, A. et al., "Molecular evolution of an arsenate detoxification pathway and DNA shuffling," Nature Biotechnology, May 1997, pp. 436–438, vol. 15.

Crameri, A. et al., "DNA shuffling of a family of genes from diverse species accelerates direct evolution," Nature, Jan. 15, 1998, pp. 288–291, vol. 391.

Duvick, J. et al., "Detoxification of mycotoxins in plants as a strategy for improving grain quality and disease resistance: Identification of fumonisin–degrading microbes from maize," Molecular Genetics of Host–Specific Toxins in Plant Disease, Proceedings of the 3rd Tottori International Symposium Daisen, Tottori, Japan, Aug. 24–29, 1997, pp. 369–381, Kluwer Academic Press, Dordrect.

Haramaya, S., "Artificial evolution by DNA shuffling," Trends in Biotechnology, Feb. 2, 1998, pp. 76–82, vol. 16(2).

Kimura, M. et al., "Trichothecene 3–O acetyltransferase protects both the producing organism and transformed yeast from related mycotoxins. cloning and characterization of Tri101," Journal of biological Chemistry, Jan. 16, 1998, pp. 1654–1661, vol. 273(3).

Pompon, D. et al., "Protein Engineering by CDNA recombination in yeasts: Shuffling of mammalian cytochrome P–450 functions," Gene, Nov. 15, 1989, pp. 15–24, vol. 83(1).

Shimoji, M. et al., "Design of a Novel P450: A functional bacterial–human cytochrome P450 chimera," Biochemistry, 1998, pp. 8848–8852, vol. 37(25).

\* cited by examiner

US 6,500,639 B2

DNA SHUFFLING TO PRODUCE NUCLEIC ACIDS FOR MYCOTOXIN DETOXIFICATION

CROSS REFERENCE TO RELATED APPLICATIONS

The present application is a non-provisional of "DNA SHUFFLING TO PRODUCE NUCLEIC ACIDS FOR MYCOTOXIN DETOXIFICATION" by Subramanian, U.S. Ser. No. 60/103,441, filed Oct. 7, 1998.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

This invention pertains to the shuffling of nucleic acids to achieve or enhance mycotoxin detoxification, especially in plants.

BACKGROUND OF THE INVENTION

"Mycotoxins" generically refer to a number of toxic molecules produced by fungal species, such as polyketides (including aflatoxins, demethylsterigmatocystin, O-methylsterigmatocystin etc.), fumonisins, alperisins (e.g., $A_1$, $A_2$, $B_1$, $B_2$), sphingofungins (A, B, C and D), trichothecenes, fumifungins, and the like. Polyketides are a large structurally diverse class of secondary metabolites synthesized by bacteria, fungi, and plants and are formed by a polyketide synthase (PKS) through the sequential condensation of small carboxylic acids. Katz and Donandio (1993) *Annu Rev. Microbiool.* 47:875–912; Brown et al. (1996) *PNAS* 93:14873–14877; Silva et al. (1996) *J. Biol Chem.* 271:13600–608.

Aflatoxin B1, is the principal member of the aflatoxin (AF) family of polyketide mycotoxins produced by *Aspergillus parasiticus, Aspergillus flavus* and *Aspergillus nomius*. Aflatoxin B1 is the most potent mycotoxin known to man. For example, AF was characterized as the causative agent for the death of more than a hundred thousand poultry in England that had ingested AF-contaminated peanut meal. This discovery led to legislation regulating the trade of AF-contaminated agricultural commodities.

Sterigniatocystin (ST) is a related polyketide mycotoxin, which is produced by several members of the Aspergillus. ST is the second to last intermediate in the biosynthesis of AF. Kelkar et al. (1997) *J. Biol Chem.* 272: 1589–94. Various Aspergillus species that produce AF and ST are known to be pathogenic to corn, grains and nuts and are known to produce these mycotoxins during the growth of the crops and during storage, leading to the introduction of AF and ST into primary food stuffs. AF and ST are acutely toxic and carcinogenic and are a serious concern from human and animal health perspective. Busby & Wogan (1985) in *Chemical Carcinogens* (Searle ed., 1985) pp 945–1136, American Chemical Society, Washington D.C.

Trichothecenes are another family of sesquiterpenoid mycotoxins produced by Fusarium species and other molds that are known plant pathogens. These compounds are potent inhibitors of protein synthesis in eukaryotes (Kimura et al. (1998) *J. Biol Chem.* 273: 1654–1661) and reportedly bind to the 60S ribosomal subunits to prevent polypeptide chain initiation or elongation. Trichothecenes are also an important group of mycotoxins that cause serious problems of food pollution. They have been implicated in incidents of mycotoxicosis including vomiting, dermatitis and hemorrhagic septicemia in humans and livestock, resulting in loss of productivity and even death. Lastly, fumonisins (F) are another structurally distinct class of mycotoxins produced by several Fusarium species that is involved in food poisoning and toxic effects. Scott (1993) *International Journal of Food Microbiology* 18:257–270 and the references therein provide a review of the Fuminosins.

Thus, the contamination of corn, grains and nuts with various types of mycotoxins produced by pathogenic species such as Aspergillus and Fusarium is a major health and food pollution problem, as well as causing reduction in crop yields by being toxic to infected plants. These mycotoxins survive food processing, which adds to the problem. It is well known that ST and AF induce liver cancer and are linked to a specific mutation in a tumor suppressor gene. Brown et al. (1996) *PNAS* 93: 14873–14877. Natural aflatoxins and other mycotoxins like ST do not pose a major health threat per se; however, renal and hepatic oxidative detoxification of these compounds in contaminated foods by cytochrome P450 enzymes yields an epoxide which is cytotoxic.

For example, AFB1 is converted to its 15,16-exo-epoxide, which is a highly toxic mutagen. Silva et al. (1996), supra and references therein. It has been shown that this epoxide targets guanine residues and selectively alkylates the N-7 position of this purine in double-stranded DNA. Depurination of the alkylated base has been correlated to bladder cancer in laboratory mice, teratogenic effects in chicken embryos and liver cancer in humans. A direct correlation between DNA damage and human cancer has been established and is related to the mutational hot spots of p53, an important tumor suppressor gene. Approximately 50% of all cancers have associated altered p53 sequences.

Trading of AF-contaminated agricultural commodities is tightly regulated at both national and international levels. Compliance to these regulations causes the loss of millions of dollars in agricultural produce in US each year. Trade sanctions and health effects on mycotoxin contaminated grains add significantly to the losses (Brown et al. (1996) *PNAS* 93: 14873–14877).

Accordingly, it is highly desirable to transform various mycotoxins produced by fungal pathogens in various crops into inactive compounds with respect to plant, human and animal toxicity. This would alleviate important food pollution problems, as well as cost associated with complying with detecting AF-contamination in various crop commodities and destroying them. Surprisingly, the present invention provides for the detoxification of mycotoxis by transformation of the mycotoxins into non-toxic compounds. This detoxification is particularly useful in crops, thereby solving each of the problems outlined above, as well as providing a variety of other features which will be apparent upon review.

SUMMARY OF THE INVENTION

In the present invention, DNA shuffling is used to generate new or improved mycotoxin detoxification genes. These mycotoxin detoxification genes are used to provide enzymes which degrade mycotoxins, in agricultural and industrial processes. These new and/or improved genes have surprisingly superior properties as compared to naturally occurring mycotoxin detoxification genes.

In the methods for obtaining mycotoxin resistant genes, a plurality of parental forms (homologs) of a selected nucleic acid are recombined. The selected nucleic acid is derived either from one or more parental nucleic acid(s) which encodes an enzyme which degrades or modifies a mycotoxin, or a fragment thereof, or from a parental nucleic acid which does not encode mycotoxin detoxification, but which is a substrate for DNA shuffling to develop monooxygenase activity. The plurality of forms of the selected nucleic acid differ from each other in at least one (and typically two or more) nucleotides, and, upon recombination, provide a library of recombinant mycotoxin detoxification nucleic acids. The library can be an in vitro set of molecules, or present in cells, phage or the like. The library is screened to identify at least one recombinant mycotoxin detoxification nucleic acid that exhibits distinct or improved mycotoxin detoxification activity (typically in an encoded polypeptide) compared to the parental nucleic acid or nucleic acids.

In selecting for mycotoxin detoxification activity, a candidate shuffled DNA can be tested for encoded mycotoxin detoxification activity in essentially any process. Common processes that can be screened include screening for inactivation or modification of an aflatoxin, inactivation or modification of a sterigmatocystin, inactivation or modification of a trichothecene, and inactivation or modification of a fumonisin. Similarly, instead of, or in addition to, testing for an increase in mycotoxin detoxification activity, it is also desirable to screen for shuffled nucleic acids which produce higher levels of a mycotoxin detoxification nucleic acid or enhanced or reduced recombinant mycotoxin detoxification polypeptide expression, or increased stability encoded by the recombinant mycotoxin resistant nucleic acid.

A variety of screening methods can be used to screen a library, depending on the mycotoxin detoxification activity for which the library is selected. By way of example, the library to be screened can be present in a population of cells. The library is selected by growing the cells in or on a medium comprising the mycotoxin to be degraded and selecting for a detected physical difference between, e.g., oxidized or reduced forms of the mycotoxin and the non-oxidized or reduced form of the mycotoxin, either in the cell, or the extracellular medium. Alternately, survival of library cells on a medium which includes a mycotoxin can be used to screen the library.

Iterative selection for mycotoxin detoxification nucleic acids is also a feature of the invention. In these methods, a selected nucleic acid identified as encoding mycotoxin detoxification activity can be shuffled, either with the parental nucleic acids, or with other nucleic acids (e.g., mutated forms of the selected nucleic acid) to produce a second shuffled library. The second shuffled library is then selected for one or more form of mycotoxin detoxification activity, which can be the same or different than the mycotoxin detoxification activity previously selected.

This process can be iteratively repeated as many times as desired, until a nucleic acid with optimized or desired mycotoxin detoxification properties is obtained. If desired, any nucleic acid identified by any of the methods herein can be cloned and, optionally, expressed. Because of the need to reduce mycoxin pollution/contamination of foods, it is desirable to express mycotoxin detoxification nucleic acids in, e.g., plants, thereby reducing the occurrence of mycotoxins in the plants. Furthermore, mycotoxin detoxification in plants also adds to the vigor of the plants.

The invention also provides methods of increasing mycotoxin detoxification activity by whole genome shuffling. In these methods, a plurality of genomic nucleic acids are shuffled in a cell (in whole cell shuffling, entire genomes are shuffled, rather than specific sequences, although "spiking" of selected nucleic acids can be used to bias shuffling outcomes). The resulting shuffled nucleic acids are selected for one or more mycotoxin detoxification traits. The genomic nucleic acids can be from a species or strain different from the cell in which activity is desired. Similarly, the shuffling reaction can be performed in cells using genomic DNA from the same or different species, or strains. Strains or enzymes exhibiting enhanced activity can be identified.

The distinct or improved activity encoded by a nucleic acid identified after shuffling can encode one or more of a variety of properties, including, e.g., inactivation or modification of a polyketide, an aflatoxin, inactivation or modification of a sterigmatocystin, inactivation or modification of a trichothecene, inactivation or modification of a fumonisin, an increased ability to chemically modify a mycotoxin, an increase in the range of mycotoxin substrates which the distinct or improved nucleic acid operates on, an increased expression level of a polypeptide encoded by the nucleic acid, a decrease in susceptibility of a polypeptide encoded by the nucleic acid to protease cleavage, a decrease in susceptibility of a polypeptide encoded by the nucleic acid to high or low pH levels, a decrease in susceptibility of the protein encoded by the nucleic acid to high or low temperatures, and a decrease in toxicity to a host cell of a polypeptide encoded by the selected nucleic acid.

The selected nucleic acids to be shuffled can be from any of a variety of sources, including synthetic or cloned DNAs. Exemplar targets for recombination include: nucleic acids encoding a monooxygenase, a P450, trichothecene-3-O-acetyltransferase, a 3-O-Methyltransferase, a glutathione S-transferase, an epoxide hydrolase, an isomerase, a macrolide-O-acytyltransferase, a 3-O-acytyltransferase, and a cis-diol producing monooxygenase which is specific for furan. Typically, shuffled nucleic acids are cloned into expression vectors to achieve desired expression levels.

One feature of the invention is the production of libraries and shuffling mixtures for use in the methods as set forth above. For example, a phage display library comprising shuffled forms of a nucleic acid is provided. Similarly, a shuffling mixture comprising at least three homologous DNAs, each of which is derived from a nucleic acid encoding a polypeptide or polypeptide fragment, is provided. These polypeptides can be, for example, any of those noted herein.

Isolated nucleic acids identified by selection of the libraries in the methods above are also a feature of the invention, as are kits comprising any of: mycotoxin detoxification nucleic acid libraries, shuffled mycotoxin detoxification nucleic acids, instructional materials for practicing any of the methods herein, containers for holding other kit components, and the like.

BRIEF DESCRIPTION OF THE FIGURES

Not Applicable.

DEFINITIONS

Unless clearly indicated to the contrary, the following definitions supplement definitions of terms known in the art.

A "recombinant monooxygenase nucleic acid" is a recombinant nucleic acid encoding a protein or RNA which confers monooxygenase activity to a cell when the nucleic acid is expressed in the cell.

A "recombinant" nucleic acid is a nucleic acid produced by recombination between two or more nucleic acids, or any nucleic acid made by an in vitro or artificial process. The term "recombinant" when used with reference to a cell indicates that the cell comprises (and optionally replicates) a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell where the genes are modified and re-introduced into the cell by artificial means. The term also encompasses cells that contain a nucleic acid endogenous to the cell that has been artificially modified without removing the nucleic acid from the cell; such modifications include those obtained by gene replacement, site-specific mutation, and related techniques.

A "recombinant mycotoxin detoxification nucleic acid" is a recombinant nucleic acid encoding a protein or RNA which confers mycotoxin detoxification or degradation activity to a cell when the nucleic acid is expressed in the cell (and, most typically, translated into a polypeptide).

A "plurality of forms" of a selected nucleic acid refers to a plurality of homologs of the nucleic acid. The homologs can be from naturally occurring homologs (e.g., two or more homologous genes) or by artificial synthesis of one or more nucleic acids having related sequences, or by modification of one or more nucleic acid to produce related nucleic acids. Nucleic acids are homologous when they are derived, naturally or artificially, from a common ancestor sequence. During natural evolution, this occurs when two or more descendent sequences diverge from a parent sequence over time, i.e., due to mutation and natural selection. Under artificial conditions, divergence occurs, e.g., in one of two ways. First, a given sequence can be artificially recombined with another sequence, as occurs, e.g., during typical cloning, to produce a descendent nucleic acid. Alternatively, a nucleic acid can be synthesized de novo, by synthesizing a nucleic acid which varies in sequence from a given parental nucleic acid sequence.

When there is no explicit knowledge about the ancestry of two nucleic acids, homology is typically inferred by sequence comparison between two sequences. Where two nucleic acid sequences show sequence similarity it is inferred that the two nucleic acids share a common ancestor. The precise level of sequence similarity required to establish homology varies in the art depending on a variety of factors. For purposes of this disclosure, two sequences are considered homologous where they share sufficient sequence identity to allow direct recombination to occur between two nucleic acid molecules (as opposed to recombination using oligonucleotide intermediates, which does not require sequence similarity to acheive recombination). Typically, nucleic acids require regions of close similarity spaced roughly the same distance apart to permit recombination to occur. The recombination can be in vitro or in vivo.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a monooxygenase, or the amino acid sequence of the monooxygenase) refers to two or more sequences or subsequences that have at least about 60%, preferably 80%, most preferably 90–95% nucleotide or amino acid residue identity, when compared and aligned for maximum correspondence, as measured using one of the following sequence comparison algorithms or by visual inspection. Such "substantially identical" sequences are typically considered to be homologous. Preferably, the "substantial identity" exists over a region of the sequences that is at least about 50 residues in length, more preferably over a region of at least about 100 residues, and most preferably the sequences are substantially identical over at least about 150 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical/homologous is that the two molecules hybridize to each other under stringent conditions. The phrase "hybridizing specifically to," refers to the binding, duplexing, or hybridizing of a molecule only to a particular nucleotide sequence under stringent conditions, including when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization conditions" and "stringent hybridization wash conditions" in the context of nucleic acid hybridization experiments such as Southern and northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays," Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but no to unrelated sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra., for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization.

A further indication that two nucleic acid sequences or polypeptides are substantially identical/homologous is that the polypeptide encoded by the first nucleic acid is immunologically cross reactive with, or specifically binds to, the polypeptide encoded by the second nucleic acid. Thus, a polypeptide is typically substantially identical to a second polypeptide, for example, where the two peptides differ only by conservative substitutions.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton (1984) *Proteins*, W. H. Freeman and Company.

In addition, individual substitutions, deletions or additions which alter, add or delete a single amino acid or a small percentage of amino acids in an encoded sequence are also "conservatively modified variations." Sequences that differ by conservative variations are generally homologous.

A "subsequence" refers to a sequence of nucleic acids or amino acids that comprise a part of a longer sequence of nucleic acids or amino acids (e.g., polypeptide) respectively.

The term "gene" is used broadly to refer to any segment of DNA associated with expression of a given RNA or protein. Thus, genes include regions encoding expressed RNAs (which typically include polypeptide coding sequences) and, often, the regulatory sequences required for their expression. Genes can be obtained from a variety of sources, including cloning from a source of interest or synthesizing from known or predicted sequence information, and may include sequences designed to have desired parameters.

The term "isolated", when applied to a nucleic acid or protein, denotes that the nucleic acid or protein is essentially free of other cellular components with which it is associated in the natural state.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19: 5081; Ohtsuka et al. (1985) J. Biol. Chem. 260: 2605–2608; Cassol et al. (1992); Rossolini et al. (1994) Mol. Cell. Probes 8: 91–98). The term nucleic acid is generic to the terms "gene", "DNA," "cDNA", "oligonucleotide," "RNA," "mRNA," and the like.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

A nucleic acid is "operably linked" when it is placed into a functional relationship with another nucleic acid sequence. For instance, a promoter or enhancer is operably linked to a coding sequence if it increases the transcription of the coding sequence.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

DETAILED DISCUSSION OF THE INVENTION

It is highly desirable to enzymatically transform various mycotoxins produced by fungal pathogens, into inactive compounds with respect to plant, human and animal toxicity. This eliminates reductions in crop yield and subsequent food pollution by mycotoxins, as well as costs associated with complying with detecting AF-contamination in various crop commodities and destroying them.

Polyketides are synthesized in fungi, e.g., by polyketide synthase. The enzyme facilitates the reiterative condensation of simple carboxylic acids; typically, acetyl-COA as a starter unit and malonyl-CoA serves as an extender unit. The biosynthetic pathway for AF and ST is, approximately, as follows: a hexanoate starter unit is converted into an initial polyketide precursor (octaketide) which is converted into norsolorinc acid, which is converted into averantin, which is converted into averufanin, which is converted into averufm, which is converted into versi-conal hemiacetal acetate, which is converted into versicolorin B, which is converted into versicolorin A, which is converted into demethylsterigmatocystin, which is converted into ST, which is converted into O-methylsterigmatocystin, which is converted into $AFB_1$. See, Yu (1995) Journal of Bacteriology 177(16):4792–4800 and the references cited therein, and Silva (1996) JBC 271(23):13600–13608 and the references cited therein.

The chemical structures of the important mycotoxin polyketides Aflatoxin $B_1$, and compounds in the biosynthetic pathway for Aflatoxin $B_1$, including sterigmatocystins, norisolornic acid, and a variety of other compounds can be found, e.g., in Silva et al. (1996) JBC 271:23:13600–13608 and the references cited therein.

The double bond at carbon atoms 15,16 of $AFB_1$ is very important with respect to toxicity (Silra et al., 1996, id). This double bond is also susceptible to oxidations such as hydroxylation, epoxidation etc. These are monooxygenase catalyzed reactions. A number of monooxygenases, including P450s (see Ortiz de Montellano (ed.) 1995, Cytochrome P450 Structure and Mechanism and Biochemistry, Second Edition Plenum Press (New York and London), monooxygenase from P. oleovorans (J. Biol. Chem., 248, 1725–1730, 1973; May J. Am. Chem. Soc., 98, 7856–7858) and other homologous non-heme iron-sulfur monooxygenases from Rhodococcus, Mycobacterium, ocardia, Pseudomonas and Bacillus; heme-dependent peroxidases, iron-sulfur monooxygenases and quinone-dependent monooxygenases are known and can be recombined in the methods herein to provide mycotoxin resistant nucleic acids. Many of these detoxification enzymes confer increased hydrophillicity to the mycotoxin, thereby facilitating excretion, e .g., in mammals.

P450s are particularly preferred monooxygenases herein. P450s are a superfamily of enzymes capable of catalyzing a wide variety of reactions including epoxidation, hydroxylation, O-dealkylations, desaturation etc. As discussed herein, one way of eliminating the toxicity of AF and ST, trichothecenes (T) and fumonisins (F) is to shuffle and select for a monooxygenase such as P450 which is capable of oxidation of mycotoxins. In one preferred embodiment, this monooxygenase nucleic acid is transduced into crop plants to make the plants mycotoxin resistant. With respect to AF, oxidation at the 15,16 position provides detoxification. Oxidative changes in other positions (for example, O-demethylation of the methoxy group in position 8, see, Silva et al. 1996) also help render the molecule nontoxic.

One particularly preferred source of p450 nucleic acids for shuffling is the cyp 1, 2 and 3 families of genes, e.g., from humans. See, http://drnelson.utmem.edu/homepage.html. A feature of the invention is the discovery that these genes display mycotoxin detoxification activity, making them especially suitable targets for recombination to develop improved detoxification properties.

While much of the discussion below deals explicitly with P450 monoxygenases, this is largely for clarity of illustration. The discussion is representative of the recombination strategies and chemistries and improvements which can be made to the structurally and functionally similar peroxidases and chlorperoxidases, as well as to the structurally unrelated iron-sulfur methane monooygenases, trichothecene-3-O-acetyltransferase, 3-O-Methyltransferase, glutathione S-transferase, epoxide hydrolases, isomerases, macrolide-O-acytyltransferases, 3-O-acytyltransferases, and cis-diol producing monooxygenases for furan, as well as for non-monooxygenase genes which can catalyze detoxification reactions such as epoxidations, hydroxylations, O-dealkylations, desaturations, etc.

Gene shuffling and family shuffling provide two of the most powerful methods available for improving and "migrating" (gradually changing the type of reaction, substrate or activity of a selected enzyme) the functions of biocatalysts. In family shuffling, homologous sequences, e.g., from different species or chromosomal positions, are recombined. In gene shuffling, a single sequence is mutated or otherwise altered and then recombined.

The generation and screening of high quality shuffled libraries provides for DNA shuffling (or "directed evolution"). The availability of appropriate high-throughput analytical chemistry to screen the libraries permits integrated high-throughput shuffling and screening of the libraries to achieve a desired mycotoxin detoxification activity.

The invention provides significant advantages over previously used methods for optimization of mycotoxin detoxification genes. For example, DNA shuffling can result in optimization of a desirable property even in the absence of a detailed understanding of the mechanism by which the particular property is mediated. In addition, entirely new properties can be obtained upon shuffling of DNAs, i.e., shuffled DNAs can encode polypeptides or RNAs with properties entirely absent in the parental DNAs which are shuffled. Indeed, even non-functional DNA sequences such as pseudo genes can be shuffled, particularly with homologous functional genes, to achieve new substrate specificity and activity.

Sequence recombination can be achieved in many different formats and permutations of formats, as described in further detail below. These formats share some common principles.

The targets for modification, vary in different applications, as does the property sought to be acquired or improved. Examples of candidate targets for acquisition of a property or improvement in a property include genes that encode proteins which have enzymatic or other activities useful in monooxygenase or other detoxification reactions.

The methods use at least two variant forms of a starting target. The variant forms of candidate substrates can show substantial sequence or secondary structural similarity with each other, but they should also differ in at least one and preferably at least two positions. The initial diversity between forms can be the result of natural variation, e.g., the different variant forms (homologs) are obtained from different individuals or strains of an organism, or constitute related sequences from the same organism (e.g., allelic variations), or constitute homologs from different organisms (interspecific variants). Alternatively, initial diversity can be induced, e.g., the variant forms can be generated by error-prone transcription, such as an error-prone PCR or use of a polymerase which lacks proof-reading activity (see, Liao (1990) Gene 88:107–111), of the first variant form, or, by replication of the first form in a mutator strain (mutator host cells are discussed in further detail below, and are generally well known). The initial diversity between substrates is greatly augmented in subsequent steps of recombination for library generation.

A mutator strain can include any mutants in any organism impaired in the functions of mismatch repair. These include mutant gene products of mutS, mutT, mutH, mutL, ovrD, dcm, vsr, umuC, umuD, sbcB, recJ, etc. The impairment is achieved by genetic mutation, allelic replacement, selective inhibition by an added reagent such as a small compound or an expressed antisense RNA, or other techniques. Impairment can be of the genes noted, or of homologous genes in any organism.

The properties or characteristics that can be acquired or improved vary widely, and, of course depend on the choice of substrate. For example, for monooxygenase genes, properties that one can improve include, but are not limited to, increased range of monooxygenases activity encoded by a particular detoxification gene, increased potency against a mycotoxin target, increased expression level of the detoxification gene, increased tolerance of the protein encoded by the detoxification gene to protease degradation (or other natural protein or RNA degredative processes), increased detoxification activity ranges for conditions such as heat, cold, low or high pH, and reduced toxicity to the host cell.

At least two variant forms of a nucleic acid which can confer mycotoxin detoxification activity are recombined to produce a library of recombinant monooxygenase genes. The library is then screened to identify at least one recombinant gene that is optimized for the particular property or properties of interest.

Often, improvements are achieved after one round of recombination and selection. However, recursive sequence recombination can also be employed to achieve still further improvements in a desired property, or to bring about new (or "distinct") properties. Recursive sequence recombination entails successive cycles of recombination to generate molecular diversity. That is, one creates a family of nucleic acid molecules showing some sequence identity to each other but differing in the presence of mutations. In any given cycle, recombination can occur in vivo or in vitro, intracellularly or extracellularly. Furthermore, diversity resulting from recombination can be augmented in any cycle by applying prior methods of mutagenesis (e.g., error-prone PCR or cassette mutagenesis) to either the substrates or products for recombination.

A recombination cycle is optionally followed by at least one cycle of screening or selection for molecules having a desired property or characteristic. Recombination cycles can also be repeated prior to selection to increase the diversity of a set of recombinant nucleic acids prior to selection. If a recombination cycle is performed in vitro, the products of recombination, i.e., recombinant segments, are sometimes introduced into cells before the screening step. Recombinant segments can also be linked to an appropriate vector or other regulatory sequences before screening. Alternatively, products of recombination generated in vitro are sometimes packaged in viruses (e.g., bacteriophage) before screening. If recombination is performed in vivo, recombination products can sometimes be screened in the cells in which recombination occurred. In other applications, recombinant segments are extracted from the cells, and optionally packaged as viruses, before screening.

The nature of screening or selection depends on what property or characteristic is to be acquired or the property or characteristic for which improvement is sought, and many examples are discussed below. It is not usually necessary to understand the molecular basis by which particular products of recombination (recombinant segments) have acquired new or improved properties or characteristics relative to the starting substrates. For example, a mycotoxin detoxification gene can have many component sequences each having a different intended role (e.g., coding sequence, regulatory sequences, targeting sequences, stability-conferring sequences, subunit sequences and sequences affecting integration). Each of these component sequences can be varied and recombined simultaneously. Screening/selection can then be performed, for example, for recombinant segments that have increased ability to confer mycotoxin detoxification activity upon a cell without the need to attribute such improvement to any of the individual component sequences of the vector.

Depending on the particular screening protocol used for a desired property, initial round(s) of screening can sometimes be performed using bacterial cells due to high transfection efficiencies and ease of culture. However, especially for eukaryotic mycotoxin detoxification enzymes such as eukaryotic P450s, yeast, fungal or other eukaryotic systems are optionally used for library expression and screening. Similarly other types of screening which are not amenable to screening in bacterial or simple eukaryotic library cells, are performed in cells selected for use in an environment close to that of their intended use. Final rounds of screening can be performed in the precise cell type of intended use.

If further improvement in a property is desired, at least one, and usually a collection, of recombinant segments surviving a first round of screening/selection are subject to a further round of recombination. These recombinant segments can be recombined with each other or with exogenous segments representing the original substrates or further variants thereof. Again, recombination can proceed in vitro or in vivo. If the previous screening step identifies desired recombinant segments as components of cells, the components can be subjected to further recombination in vivo, or can be subjected to further recombination in vitro, or can be isolated before performing a round of in vitro recombination. Conversely, if the previous screening step identifies desired recombinant segments in naked form or as components of viruses, these segments can be introduced into cells to perform a round of in vivo recombination. The second round of recombination, irrespective how performed, generates further recombinant segments which encompass additional diversity than is present in recombinant segments resulting from previous rounds.

The second round of recombination can be followed by a further round of screening/selection according to the principles discussed above for the first round. The stringency of screening/selection can be increased between rounds. Also, the nature of the screen and the property being screened for can vary between rounds if improvement in more than one property is desired or if acquiring more than one new property is desired. Additional rounds of recombination and screening can then be performed until the recombinant segments have sufficiently evolved to acquire the desired new or improved property or function.

The practice of this invention can be exploited to select for mutants which retain activity under conditions of interest. Such conditions include but are not limited to: different pH optima, broader pH optima, activity in altered solvents such as DMSO (Seto et al., DNA Sequence 5:131–140 (1995)) or forimamide (Chen et al., Proc. Natl. Acad. Sci. (U.S.A.) 90:5618–5622, (1993)) altered temperature, improved shelf life, altered or broadened substrate specificity, or protease resistance. For example, recursive sequence recombination is ideally suited to evolving enzymes for catalysis under conditions where salt concentrations or pH were different from the original enzyme optimas.

The practice of this invention involves the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well-known to persons of skill. General texts which describe molecular biological techniques useful herein, including mutagenesis, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1998) ("Ausubel")). Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426, 039. Improved methods of amplifying large nucleic acids by PCR are summarized in Cheng et al. (1994) *Nature* 369: 684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausbel, Sambrook and Berger, all supra.

Oligonucleotides for use as probes, e.g., in in vitro amplification methods, for use as gene probes, or as shuffling targets (e.g., synthetic genes or gene segments) are typically synthesized chemically according to the solid phase phosphoramidite triester method described by Beaucage and Caruthers (1981), *Tetrahedron Letts.*, 22(20):1859–1862, e.g., using an automated synthesizer, as described in Needham-VanDevanter et al. (1984) *Nucleic Acids Res.*, 12:6159–6168. Oligonucleotides can also be custom made and ordered from a variety of commercial sources known to persons of skill.

Indeed, essentially any nucleic acid with a known sequence can be custom ordered from any of a variety of commercial sources, such as The Midland Certified Reagent Company, The Great American Gene Company, ExpressGen Inc., Operon Technoloigies Inc. (Alameda, Calif.) and many others. Similarly, peptides and antibodies can be custom ordered from any of a variety of sources, such as PeptidoGenic, HTI Bio-products, inc., BMA Biomedicals Ltd (U.K.), Bio Synthesis, Inc., and many others.

Family Shuffling Mycotoxin Detoxification Genes

A large number of P450 genes are known. This makes P450 genes ideal substrates for family shuffling (any of the other genes for mycotoxin detoxification which are discussed supra are For identification of homologous genes used in family shuffling strategies, representative alignments of P450 enzymes can be found in the Appendices of the volume *Cytochrome P450: Structure, Mechanism, and Biochemistry*, $2^{nd}$ Addition (ed. By Paul R. Ortiz de Montellano) Plenum Press, New York, 1995) ("Ortiz de Montellano"). An up-to-date list of P450s can be fond electronically on the World Wide Web (http://www.drnelson.utmem.edu/homepage.html).

To illustrate the family shuffling approach to improving P450 enzymes (essentially similar approaches apply to other mycotoxin detoxification nucleic acids), one or more of the more than 1000 members of this superfamily is/are selected, aligned with similar homologous sequences, and shuffled against these homologous sequences.

An example P450 which can be shuffled by any of the procedures herein is the *Aspergillus nidulans* stcL gene, which encodes a cytochrome P450 monooxygenase required for bisfuran desaturation during aflatoxin/sterigmatocystin biosynthesis. See, Kelkar et al (1997) *JBC* 1589–1594 for a description of the structure and function of the stcl gene.

Similarly, gene sequences for other monooxygenases, trichothecene-3-O-acetyltransferase, a 3-O-Methyltransferase, a glutathione S-transferase, epoxide hydrolases, isomerases, macrolide-O-acytyltransferases, 3-O-acytyltransferases, and cis-diol producing monooxygenases specific for furan are all well illustrated in the literature and in, e.g., publicly available sequence repositories such as Genbank.

For example, Trichothecene mycotoxins such as deoxynivalenol, 4,15-diacetoxyscripenol and T-2 toxin are all potent protein synthesis inhibitors for eukaryotic organisms. The 3-O-acetyl derivatives of these toxins have significantly lower toxic activity. Tri101, a gene responsible for 3-O-acetylation reactions was cloned from a *Fusarium graminearum* cDNA library. See, Kimura et al. (1997) *JBC* 273(3):1654–1661 for a description of the gene sequence. Kimura et al. cloned the Tri101 cDNA for expression in yeast and selected for 3-O-acetylation in the presence of T-2 toxin. See, id. The Tri101 gene can be shuffled by any of the procedures herein. The gene specifying this enzyme codes a 451-amino acid protein, which is unique (Kimura et al. 1998). This gene can be shuffled for improvement of activity as well as broadening specificity with respect to acetylation of hydroxyl groups in other mycotoxins like ST and F. The selection system for T and other mycotoxins that are protein synthesis inhibitors is straight forward. Yeast is susceptible to these toxins and any transformed yeast capable of acetylating the toxins will be viable (Kimura et al. 1998).

Other sources of genes for shuffling include those catalyzing N-acetylation, O-glycosylation and O-phosphorylation. These are mechanisms of inactivation of representatives of various antibiotics and herbicides. Genes specifying these activities can be shuffled both for improvement of activity and specificity with respect to compounds like T and ST and F. The gene or genes optimized for any of the above transferase activity can be cloned into desired crops in order to detoxify one or more pathogen-derived mycotoxins.

Other genes for detoxification of mycotoxins include the 3-O-Methyltransferases (MT). These enzymes provide for irreversible modification to ether. MTs are typically single polypeptides with no redox cofactors. Selection in yeast is used to evolve and screen as that used for cloning of 3-OAT specific for mycotoxins of the family T. T2 (or related 3-deacetyl derivative) is used with radioactive (Methyl) labeled SAM to screen for source organisms capable of modifying T2.

Another candidate for DNA-shuffling to inactivate various mycotoxins is the gene coding for macrohalide-O-acyltransferase such as 3-O-acyltransferase (Hara and Hutchinson (1992) *J. Bacteriol.* 174: 5141–5144. This gene is shuffled individually or in combination with its homologs for the desired activity with mycotoxins.

Targets for shuffling to acquire mycotoxin detoxification properties also include mycotoxin synthetic genes such as polyketide synthases. These synthetic genes could be modified by shuffling to catalyze reverse synthetic reactions to break down the polyketides they ordinarily produce. An example target is the pksST gene from *Aspergillus nidulans*, which is necessary for the synthesis of ST. Yu and Leonard (1995) *Journal of Bacteriology* 177(16):4792–4800 describe the structure and function of the pksST gene. Similarly, the pksL gene required for aflatoxin biosynthesis in *Aspergillus parasiticus* is described by Feng and Leonard *Journal of Bacteriology* 177(21):6246–6254. Another example is Versicolorin B synthase, which synthesizes the side chain cyclization of racemic versiconal hemiacetal to the bisfuran ring system of versicolorin B. The dihydrobisfuran is important to the mutagenic nature of $AFB_1$ and ST. The isolation and characterization of the Versicolorin B synthase gene from *Aspergillus parasiticus* and the partial characterization of the related synthetic cluster is described in Silva (1996) *JBC* 271(23):13600–13608. A total of twenty five co-regulated transcripts defining a ST gene cluster, and containing most, or all, of the genes necessary for ST biosynthesis in *A. nidulans* is described by Brown et al. (1996) *PNAS* 93:1418–1422. These genes are also targets for shuffling for mycotoxin detoxification. Whole genome shuffling approaches (described below) can also be used to select for plant cells which produce products that down-regulate production of genes such as those described in Brown, id. (which provide for ST and AF biosynthesis) thereby reducing ST and AF levels in target plants.

A variety of organisms known to contain additional monooxygenases which could be shuffled in the methods of the invention are also known. The most comprehensive studies on bacterial alkene epoxidation have been done on *Pseudomonas oleovorans*. Work on *P. oleovorans* by May and coworkers (*J. Biol. Chem.*, 248, 1725–1730) showed that the monoxygenase contained in the cells is capable of epoxidizing octene to 1,2-epoxy-octane in 70% enantiomeric purity. In addition, this enzyme is capable of converting 1,7-octadiene to the diepoxide (May et al, *J. Am. Chem. Soc.*, 98, 7856–7858) and 1,5-hexadiene and 1,11-dodecadiene to epoxides. This enzyme system is also capable of mediating hydroxylation of longer chain alkanes (octanes, etc.) and fatty acids. The enzyme has been cloned and sequenced and is comprised of three protein components: rubredoxin (mw 19,000), NADH-rubredoxin reductase, and the ω-hydroxylase (a non-heme iron protein). Microorganisms having MMO enzyme activities with similar properties include the genera Rhodoccous, Mycobacterium, Nocardia (*Nocardia carollina* B-276) and *Pseudomonas Corynebacterium equi* (IFO 3730). All of these strains are available from ATCC and serve as sources for the genes which can be isolated by hybridization and gene amplification methods.

Mycotoxin detoxification screening is done most easily in yeast, but a bacterial system could also be constructed by co-expressing the accessory electron transport proteins adrenodoxin and adrenodoxin reductase. DNA from clones with improved activity can be shuffled together in subsequent rounds of DNA shuffling and screened for further improvement.

Assays for Mycotoxin Inactivation

Screening a number of cloned cytochrome P450 monooxygenases for activity vs. various AF and ST and other mycotoxins yields P450 nucleic acids specifying these reactions and other oxidative changes in 15, or 16 positions (like hydroxylation). These P450 genes can be of fungal, microbial, plant, insect or mammalian origin. The screen can be conducted by measuring the activity against any particular mycotoxin or against multiple mycotoxins, e.g., by preparing extracts of clones expressing P450 genes. The expected product(s) from the above toxins as well as other oxidized products derived from a P450 can be identified based on differences in physical properties (oxidation of mycotoxins causes a detectable difference in the physical characteristics of mycotixins).

It is possible to directly select the clones expressing P450 specifying either specific or broad-based oxidation by using yeast, if the yeast are susceptible to the compound. For example, as noted above, Kimura et al (1997) describe expression of the tri101 gene in yeast and selection of the yeast in medium containing T-2 toxin, a potent mycotoxin. This same assay format can be used for any mycotoxin which is toxic to yeast, or inhibitory to yeast growth on a medium.

Similarly, such assays can be performed using any of a variety of other cultured cells, by growing the cells (e.g., prokaryotic or eukaryotic cells) in the presence of a mycotoxin. To gradually select for more and more potent mycotoxin detoxification nucleic acids, cells are grown in medium containing increasingly high doses of the mycotoxin, e.g., following each round of a reiterative DNA shuffling procedure, as described herein.

In general, the culture of cells, including yeast, animal cells, plant cells and the like are well known. In addition to Berger, Ausubel and Sambrook, all supra, details on animal cell culture can be found in Freshney (*Culture of Animal Cells, a Manual of Basic Technique,* third edition Wiley-Liss, New York (1994)) and the references cited therein. The culture of plant cells is described, e.g., in Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of Cell culture media are described in Atlas and Parks (eds) The Handbook of Microbiological Media (1993) CRC Press, Boca Raton, Fla. (Atlas). It will be appreciated that plant cells are desireably transduced with mycotoxin resistance nucleic acids to reduce food contamination by mycotoxins and to improve plant resistance to mycotoxins, e.g., to enhance yeild. Accordingly, it can be convenient to screen to mycotoxin detoxification using plant cells in culture which correspond to plants desireably transduced.

If the oxidized products of the reaction are fluorescent, clones having mycotoxin detoxification activity are detected by fluorescence of specific mycotoxins. The intensity of fluorescence may help select clones having higher activity (or higher expression).

Clones expressing shuffled mycotoxin detoxification nucleic acids can be examined for oxidation of one or more mycotoxin in pools of 10, in order to prescreen the initial transformants rapidly. Any pools showing significant activity can be deconvoluted to identify single desirable clones with high activity and/or broad specificity. The mycotoxin detoxification nucleic acid from one or more such clones could be subjected to a second and subsequent round of shuffling in order to further optimize the rate of oxidation or to broaden the mycotoxin substrate specificity.

The appropriate gene or genes optimized for rapid oxidation of one or more mycotoxins like AF, ST, T and F are optionally cloned into desired crops in order rapidly detoxify the toxin produced by the pathogen. This reduces food contamination caused by these compounds. In the case of AF and ST, even if the oxidized product were the toxic 15,16-epoxide or an equivalent derivative of the parent substrate, it would be sequestered quickly in the plants due to its instability. For example, the epoxide could be rapidly conjugated to a nucleophile or hydrolyzed or it could form a DNA-adduct. All of these derivatives, if present in the grain commodities produced from transgenic plants, are nontoxic to humans and animals.

For detection of demthylation (other than MS), free thiol or amine—bearing scintillating polymeric beads (covalent reaction with epoxy moiety) can be used. The beads are washed, radioactivity counted (only beads attached to O-methylated T2 will be counted). In a variation of assay, with non-bead scintillating material, surfaces are activated with thiols or amines. All these variations are, in essence, SPA assays.

For Glutathione S-trasferases (GSTs), the epoxide moiety of T2 is amenable to nucleophilic attack by thiol nucleophiles, including glutathione, whether transferred or not by GST. The thiol-T2 conjugate compound can be formed in an irreversible manner and is not an active toxin. Endogenous GST levels in plants are likely to be sufficient. Selection in yeast is used to evolve and screen as above for 3-OAT. DNA shuffling is used to optimize the specificity of plant GST enzymes towards T2 epoxide.

For epoxide hydrolase or isomerase it is sufficient to disrupt the T2 toxophore by modifying 12,13-epoxide to a glycol or an aldehyde. No known natural enzymes work on this epoxide. However, DNA shuffling is used to impart and optimize the required specificity. Selection in yeast is used to evolve and screen as for 3-OAT above.

Other assays for shuffling include chemical assays based on reactivity of residual epoxide, or formed rearranged 13-aldehyde product. One option is the use of a cytochrome P450 enzyme for aflatoxin detoxification by epoxidation of the double bond of the dihydrobisfuran moiety. Also, this can be used in conjunction with nucleophilic opening of the 15,16-epoxide (epoxide hydrolase, or GST, or an amine nucleophile, e.g. nucleobase or amino acid). Although 13-acetal can, in principle, be a subject to hydrolytic opening (enzymatic), the spontaneous toxophore regeneration may occur as it is favored by stereochemical means. Reactivity of 15,16-epoxide towards nucleophiles can be used for screen of P450s with the best activity towards AFB1. Exogenously supplied nucleophiles convenient for detection of AFB-epoxide-nucleophile adduct can be supplied in order to have shuffling done in bacterial or other microbial host which is insensitive to AFB1.

An alternative method for the assay of P450s with optimized activity towards aflatoxinBI can use a variation of scintillation proximity assay using beads or other SPA material activated with a suitable nucleophilic group (amine, thiol) to trap any AFB1 15,16-eopxide. This uses a radioactively labeled AFB1 as a screen substrate. The latter can be prepared by chemical means, or by means of biosynthesis (with AFB1 producing Aspergillus strains) using a radioactively labeled AFB1 precursor/intermediate of its biosynthesis pathway.

Other microbial genes specifying oxygenases suitable for oxidation of aflatoxin such as AFB1 are cis-diol making dioxygenases with specificity for furan substructures. Other genes coding for flavoprotein monooxygenases of microbial or mammalian origin are suitable candidates for shuffling for generating and improving activity vs. AF, ST and T. An way of degrading AFB1 is by opening the coumarin-lactone ring—C1 ester with a hydrolase. This is of value when the ring opening product is intercepted with a peroxidase for oxidative radical coupling of the free C12 phenol. The toxophore is destroyed after this oxidation. Even without peroxidase-induced radical oxidation process, the hydrolytic option is of use because the lactone ring opening product is subject to spontaneous C-1 hydrolytic decarboxylation (beta-ketoacid).

As is apparent from the foregoing, the relevant assay will depend on the application. Many assays formats are suitable. Advantageously, any of the assays can be practiced in a high-throughput format.

In the high throughput assays of the invention, it is possible to screen up to several thousand different shuffled variants in a single day. For example, each well of a microtiter plate can be used to run a separate assay, or, if concentration or incubation time effects are to be observed, every 5–10 wells can test a single variant. Thus, a single standard microtiter plate can assay about 100 (e.g., 96) mycotoxin detoxification reactions. If 1536 well plates are used, then a single plate can easily assay from about 100-about 1500 different reactions. It is possible to assay several different plates per day; assay screens for up to about 6,000–20,000 different assays (i.e., involving different nucleic acids, encoded proteins, concentrations, etc.) is possible using the integrated systems of the invention. More recently, microfluidic approaches to reagent manipulation have been developed, e.g., by Caliper Technologies (Palo Alto, Calif.).

In addition to fluidic approaches, it is possible simply to grow cells on plates of agar which comprise mycotoxins. Cells which have mycotoxin detoxification activity (e.g., due to transduction with mycotoxin detoxification nucleic acids) are able to grow on the plates. This approach offers a very simple and high-throughput screening method.

In one aspect, library members, e.g., cells, viral plaques, spores or the like, are separated on solid media to produce individual colonies (or plaques). Using an automated colony picker (e.g., the Q-bot, Genetix, U.K.), colonies or plaques are identified, picked, and up to 10,000 different mutants inoculated into 96 well microtiter dishes, optionally containing glass balls in the wells to prevent aggregation. The Q-bot does not pick an entire colony but rather inserts a pin through the center of the colony and exits with a small sampling of cells, (or mycelia) and spores (or viruses in plaque applications). The time the pin is in the colony, the number of dips to inoculate the culture medium, and the time the pin is in that medium each effect inoculum size, and each can be controlled and optimized. The uniform process of the Q-bot decreases human handling error and increases the rate of establishing cultures (roughly 10,000/4 hours). These cultures are then shaken in a temperature and humidity controlled incubator. The glass balls in the microtiter plates act to promote uniform aeration of cells dispersal of mycelial fragments, or the like, similar to the blades of a fermenter. Clones from cultures of interest can be cloned by limiting dilution. As also described supra, plaques or cells constituting libraries can also be screened directly for production of proteins, either by detecting hybridization, protein activity, protein binding to antibodies, or the like.

The ability to detect a subtle increase in the performance of a shuffled library member over that of a parent strain relies on the sensitivity of the assay. The chance of finding the organisms having an improvement in mycotoxin detoxification activity is increased by the number of individual mutants that can be screened by the assay. To increase the chances of identifying a pool of sufficient size, a.prescreen that increases the number of mutants processed by 10-fold can be used. The goal of the primary screen will be to quickly identify mutants having equal or better product titers than the parent strain(s) and to move only these mutants forward to liquid cell culture for subsequent analysis.

A number of well known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a scientist. Any of the above devices are suitable for use with the present invention, e.g., for high-throughput screening of molecules encoded by codon-altered nucleic acids. The nature and implementation of modifications to these devices (if any) so that they can operate as discussed herein with reference to the integrated system will be apparent to persons skilled in the relevant art.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

The manufacturers of such systems provide detailed protocols the various high throughput. Thus, for example, Zymark Corp. provides technical bulletins describing screening systems for detecting the modulation of gene transcription, ligand binding, and the like. Microfluidic approaches to reagent manipulation have also been developed, e.g., by Caliper Technologies (Palo Alto, Calif.).

Optical images viewed (and, optionally, recorded) by a camera or other recording device (e.g., a photodiode and data storage device) are optionally further processed in any of the embodiments herein, e.g., by digitizing the image and/or storing and analyzing the image on a computer. As noted above, in some applications, mycotoxin detoxification products are florescent, making optical detection approaches appropriate in these instances. A variety of commercially available peripheral equipment and software is available for digitizing, storing and analyzing a digitized video or digitized optical image, e.g., using PC (Intel x86 or pentium chip-compatible DOS™, OS2™ WINDOWS™, WINDOWS NT™ or WINDOWS95™ based machines), MACINTOSH™, or UNIX based (e.g., SUN™ work station) computers.

One conventional system carries light from the assay device to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

Integrated systems for analysis in the present invention typically include a digital computer with high-throughput liquid control software, image analysis software, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled assay component. The image scanner interfaces with the image analysis software to provide a measurement of optical intensity. Typically, the intensity measurement is interpreted by the data interpretation software to show whether the mycotoxin detoxification products are produced.

Monooxygenase activity can also be monitored by HPLC, gas chromatography and mass spectroscopy, as well as a variety of other analytical methods available to one of skill. Incorporation of $^{18}O$ from radio-labeled molecular oxygen can be monitored directly by mass shift by MS methods and by an appropriate radioisotope detector with HPLC and GC devices. In a high-throughput modality, a method of choice is high-throughput MS, or MS with an electron spray-based detection method.

In addition, epoxide formation can be indirectly measured by various reactive colorimetric reactions. For example, disappearance of peroxide over time can be monitored directly either potentiometrically or calorimetrically using a number of commercially available peroxide reactive dyes.

In one set of assays, the relative toxicity of mycotoxin products produced by modification of mycotoxin detoxification enzymes is determined. In particular, toxicity can be evaluated in any of the usual assays for mycotoxin toxicity and, optionally, compared to the toxicity of the unmodified mycotoxin. In the event that toxicity is reduced, secondary toxic effects of detoxification products can be evaluated using these usual assays for mycotoxin activity, or using additional assays such as cell survival assays, e.g., in the presence of increasing levels of the secondary product. This secondary assay helps to determine which mycotoxin detoxification activities are most desirable, i.e., using secondary toxicities of mycotoxin metabolites as a measure of unwanted toxicity.

Formats for Nucleic Acid Recombination-Nucleic Acid Shuffling

The present invention involves shuffling of nucleic acids. The following publications describe a variety of recursive recombination (shuffling) procedures and/or methods which can be incorporated into such procedures: Stemmer, et al., (1999) "Molecular breeding of viruses for targeting and other clinical properties. Tumor Targeting" 4:1–4; Nesset al. (1999) "DNA Shuffling of subgenomic sequences of subtilisin" *Nature Biotechnology* 17:893–896; Chang et al. (1999) "Evolution of a cytokine using DNA family shuffling" *Nature Biotechnology* 17:793–797; Minshull and Stemmer (1999) "Protein evolution by molecular breeding" *Current Opinion in Chemical Biology* 3:284–290; Christians et al. (1999) "Directed evolution of thymidine kinase for AZT phosphorylation using DNA family shuffling" *Nature Biotechnology* 17:259–264; Crameriet al. (1998) "DNA shuffling of a family of genes from diverse species accelerates directed evolution" *Nature* 391:288–291; Crameri et al. (1997) "Molecular evolution of an arsenate detoxification pathway by DNA shuffling," *Nature Biotechnology* 15:436–438; Zhang et al. (1997) "Directed evolution of an effective fucosidase from a galactosidase by DNA shuffling and screening" *Proceedings of the National Academy of Sciences, U.S.A.* 94:4504–4509; Patten et al. (1997) "Applications of DNA Shuffling to Pharmaceuticals and Vaccines" *Current Opinion in Biotechnology* 8:724–733; Crameri et al. (1996) "Construction and evolution of antibody-phage libraries by DNA shuffling" *Nature Medicine* 2:100–103; Crameri et al. (1996) "Improved green fluorescent protein by molecular evolution using DNA shuffling" *Nature Biotechnology* 14:315–319; Gates et al. (1996) "Affinity selective isolation of ligands from peptide libraries through display on a lac repressor 'headpiece dimer'" *Journal of Molecular Biology* 255:373–386; Stemmer (1996) "Sexual PCR and Assembly PCR" In: *The Encyclopedia of Molecular Biology*. VCH Publishers, New York. pp.447–457; Crameri and Stemmer (1995) "Combinatorial multiple cassette mutagenesis creates all the permutations of mutant and wildtype cassettes" *BioTechniques* 18:194–195; Stemmer et al., (1995) "Single-step assembly of a gene and entire plasmid form large numbers of oligodeoxyribonucleotides" *Gene,* 164:49–53; Stemmer (1995) "The Evolution of Molecular Computation" *Science* 270: 1510; Stemmer (1995) "Searching Sequence Space" *Bio/Technology* 13:549–553; Stemmer (1994) "Rapid evolution of a protein in vitro by DNA shuffling" *Nature* 370:389–391; and Stemmer (1994) "DNA shuffling by random fragmentation and reassembly: In vitro recombination for molecular evolution." *Proceedings of the National Academy of Sciences, U.S.A.* 91:10747–10751.

Additional details regarding DNA shuffling methods are found in U.S. Patents by the inventors and their co-workers, including: U.S. Pat. No. 5,605,793 to Stemmer (Feb. 25, 1997), "METHODS FOR IN VITRO RECOMBINATION;" U.S. Pat. No. 5,811,238 to Stemmer et al. (Sep. 22, 1998) "METHODS FOR GENERATING POLYNUCLEOTIDES HAVING DESIRED CHARACTERISTICS BY ITERATIVE SELECTION AND RECOMBINATION;" U.S. Pat. No. 5,830,721 to Stemmer et al. (Nov. 3, 1998), "DNA MUTAGENESIS BY RANDOM FRAGMENTATION AND REASSEMBLY;"U.S. Pat. No. 5,834,252 to Stemmer, et al. (Nov. 10, 1998) "END-COMPLEMENTARY POLYMERASE REACTION," and U.S. Pat. No. 5,837,458 to Minshull, et al. (Nov. 17, 1998), "METHODS AND COMPOSITIONS FOR CELLULAR AND METABOLIC ENGINEERING."

In addition, details and formats for DNA shuffling are found in a variety of PCT and foreign patent application publications, including: Stemmer and Crameri, "DNA MUTAGENESIS BY RANDOM FRAGMENTATION AND REASEMBLY" WO 95/22625; Stemmer and Lipschutz "END COMPLEMENTARY POLYMERASE CHAIN REACTION" WO 96/33207; Stemmer and Crameri "METHODS FOR GENERATING POLYNUCLEOTIDES HAVING DESIRED CHARACTERISTICS BY ITERATIVE SELECTION AND RECOMBINATION" WO 97/0078; Minshul and Stemmer, "METHODS AND COMPOSITIONS FOR CELLULAR AND METABOLIC ENGINEERING" WO 97/35966; Punnonen et al. "TARGETING OF GENETIC VACCINE VECTORS" WO 99/41402; Punnonen et al. "ANTIGEN LIBRARY IMMUNIZATION"

WO 99/41383; Punnonen et al. "GENETIC VACCINE VECTOR ENGINEERING" WO 99/41369; Punnonen et al. OPTIMIZATION OF IMMUNOMODULATORY PROPERTIES OF GENETIC VACCINES WO 9941368; Stemmer and Crameri, "DNA MUTAGENESIS BY RANDOM FRAGMENTATION AND REASSEMBLY" EP 0934999; Stemmer "EVOLVING CELLULAR DNA UPTAKE BY RECURSIVE SEQUENCE RECOMBINATION" EP 0932670; Stemmer et al., "MODIFICATION OF VIRUS TROPISM AND HOST RANGE BY VIRAL GENOME SHUFFLING" WO 9923107; Apt et al., "HUMAN PAPILLOMAVIRUS VECTORS" WO 9921979; Del Cardayre et al. "EVOLUTION OF WHOLE CELLS AND ORGANISMS BY RECURSIVE SEQUENCE RECOMBINATION" WO 9831837; Patten and Stemmer, "METHODS AND COMPOSITIONS FOR POLYPEPTIDE ENGINEERING" WO 9827230; Stemmer et al., and "METHODS FOR OPTIMIZATION OF GENE THERAPY BY RECURSIVE SEQUENCE SHUFFLING AND SELECTION" WO9813487.

Certain U.S. Applications provide additional details regarding DNA shuffling and related techniques, including "SHUFFLING OF CODON ALTERED GENES" by Patten et al. filed Sep. 29, 1998, (U.S. Ser. No. 60/102,362), Jan. 29, 1999 (U.S. Ser. No. 60/117,729), and Sep. 28, 1999, U.S. Ser. No. 09/407,800 (pending); "EVOLUTION OF WHOLE CELLS AND ORGANISMS BY RECURSIVE SEQUENCE RECOMBINATION", by del Cardyre et al. filed Jul. 15, 1998 (U.S. Ser. No. 09/166,188), (pending) and Jul. 15, 1999 (U.S. Ser. No. 09/354,922) U.S. Pat. No. 6,379,964; "OLIGONUCLEOTIDE MEDIATED NUCLEIC ACID RECOMBINATION" by Crameri et al., filed Feb. 5, 1999 (U.S. Ser. No. 60/118,813) and filed Jun. 24, 1999 (U.S. Ser. No. 60/141,049) and filed Sep. 28, 1999 (U.S. Ser. No. 09/408,392, U.S. Pat. No. 6,376,246); and "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393); and "METHODS FOR MAKING CHARACTER STRINGS, POLYNUCLEOTIDES & POLYPEPTIDES HAVING DESIRED CHARACTERISTICS" by Selifonov and Stemmer, filed Feb. 5, 1999 (U.S. Ser. No. 60/118854).

As review of the foregoing publications, patents, published applications and U.S. patent applications reveals, shuffling (or "recursive recombination") of nucleic acids to provide new nucleic acids with desired properties can be carried out by a number of methods. These methods can be adapted to the present invention to evolve the mycotoxin detoxification activity as discussed herein to produce new mycotoxin detoxification nucleic acids with new or improved properties. Both the methods of making such mycotoxin detoxification nucleic acids and the mycotoxin detoxification nucleic acids produced by these methods are a feature of the invention.

In brief, at least 5 different general classes of recombination methods are applicable to the present invention. First, nucleic acids can be recombined in vitro by any of a variety of techniques discussed in the references above, including e.g., DNAse digestion of nucleic acids to be recombined followed by ligation and/or PCR reassembly of the nucleic acids. Second, nucleic acids can be recursively recombined in vivo, e.g., by allowing recombination to occur between nucleic acids in cells. Third, whole cell genome recombination methods can be used in which whole genomes of cells are recombined, optionally including spiking of the genomic recombination mixtures with desired library components such as mycotoxin detoxification nucleic acids homologue nucleic acids. Fourth, synthetic recombination methods can be used, in which oligonucleotides corresponding to different mycotoxin detoxification nucleic acid homologues are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made and shuffled by tri-nucleotide synthetic and shuffling approaches. Fifth, in silico methods of recombination can be effected in which genetic algorithms are used in a computer to recombine sequence strings which correspond to mycotoxin detoxification nucleic acid homologues. The resulting recombined sequence strings are optionally converted into nucleic acids by synthesis of nucleic acids which correspond to the recombined sequences, e.g., in concert with oligonucleotide synthesis/gene reassembly techniques. Any of the preceding general recombination formats can be practiced in a reiterative fashion to generate a more diverse set of recombinant nucleic acids. In addition, these general approaches can, and often are, used in combination.

The above references provide these and other basic recombination formats as well as many modifications of these formats. Regardless of the format which is used, the nucleic acids of the invention can be recombined (with each other or with related (or even unrelated) nucleic acids to produce a diverse set of recombinant nucleic acids, including homologous nucleic acids. In general, the sequence recombination techniques described herein provide particular advantages in that they provide for recombination between mycotoxin detoxification nucleic acids, or derivatives thereof, in any available format, thereby providing a very fast way of exploring the manner in which different combinations of sequences can affect a desired result.

Following recombination, any nucleic acids which are produced can be selected for a desired activity. In the context of the present invention, this can include testing for and identifying any mycotoxin detoxification activities, by any of the assays in the art. In addition, useful properties such as low crop yield enhancement, can also be simultaneously selected for. A variety of mycotoxin detoxification nucleic acid related (or even unrelated) properties can be assayed for, using any available assay.

A recombinant nucleic acid produced by recursively recombining one or more polynucleotide of the invention with one or more additional nucleic acid also forms a part of the invention. The one or more additional nucleic acid may include another polynucleotide of the invention (i.e., one or more evolved mycotoxin detoxification nucleic acids); optionally, alternatively, or in addition, the one or more additional nucleic acid can include, e.g., a nucleic acid encoding a naturally-occurring mycotoxin detoxification nucleic acid or a subsequence thereof, or any homologous sequence or subsequence thereof, or, e.g., any other homologous or non-homologous nucleic acid (certain recombination formats noted above, notably those performed synthetically or in silico, do not require homology for recombination).

The recombining steps may be performed in vivo, in vitro, or in silico as described in more detail in the references above. Also included in the invention is a cell containing any resulting recombinant nucleic acid, nucleic acid libraries produced by recursive recombination of the nucleic acids set forth herein, and populations of cells, vectors, viruses, plasmids or the like comprising the library or comprising any recombinant nucleic acid resulting from recombination (or recursive recombination) of a nucleic acid as set forth herein with another such nucleic acid, or an additional nucleic acid. Corresponding sequence strings in a database present in a computer system or computer readable medium are a feature of the invention.

Specific Formats for Sequence Recombination

DNA shuffling can be applied to a collection of mycotoxin without prior screening for activity vs. one or more mycotoxins. The shuffled genes can be cloned in appropriate *E. coli* or yeast, and clones exhibiting desired activity can be selected as described above. The screening will be based e.g., on differences in the physical properties between the parent mycotoxin and its modified, oxidized product, or upon cell survival on mycotoxin containing media. The final gene product can be optimized for rapid oxidation and/or desired substrate specificity for one or more mycotoxins, by further rounds of shuffling. The optimized gene or genes obtained after several rounds of shuffling could be cloned into desired crops in which AF, ST or other mycotoxin production by the appropriate pathogen is a problem. This will help eliminate the toxicity associated with the pathogen-produced mycotoxins in the grains.

Shuffled gene(s) developed by the above screening method for the identification of oxidation of one or more mycotoxins are optionally shuffled by at least one of the five general apparoches for sequence recombination noted above.

In specific formats, DNA-shuffling can be performed on a single gene. Alternatively, several homologous genes can be identified by sequence comparison with known homologous genes. These genes can be synthesized and shuffled as a family of homologs, to select recombinants with the desired activity. The shuffled genes can be cloned into *E. coli,* yeast, plants, fungi, or animal cells and those producing high activity can be identified by the methods described above.

Whole genome shuffling can be performed to shuffle detoxification genes (along with other genomic nucleic acids), thereby producing cells with enhanced detoxification activity. For whole genome shuffling approaches, it is not even necessary to identify which mycotoxin detoxification genes are being shuffled. Instead, e.g., plant cell genomes are combined and shuffled to acquire mycotoxin detoxification activity, as measured in any of the assays above.

Mycotoxin detoxification genes can be codon modified to access mutational diversity not present in any naturally occurring detoxification gene. Shuffling can be performed using synthetic shuffling and in silico approaches. Details on each of these procedures can be found in the references noted above and as further detailed below.

Generally, the methods of the invention entail performing DNA recombination ("shuffling") and screening or selection to "evolve" individual genes, whole plasmids or viruses, multigene clusters, or even whole genomes (e.g., Stemmer (1995) *Bio/Technology* 13:549–553 and the other references noted herein). Reiterative cycles of recombination and screening/selection can be performed to further evolve the nucleic acids of interest. Such techniques do not require the extensive analysis and computation required by conventional methods for polypeptide engineering. Shuffling allows the recombination of large numbers of mutations in a minimum number of selection cycles, in contrast to natural pair-wise recombination events (e.g., as occur during sexual replication). Thus, the sequence recombination techniques described herein provide particular advantages in that they provide recombination between mutations in any or all of these, thereby providing a very fast way of exploring the manner in which different combinations of mutations can affect a desired result. In some instances, however, structural and/or functional information is available which, although not required for sequence recombination, provides opportunities for modification of the technique.

Exemplary formats and examples for sequence recombination, referred to, e.g., as "DNA shuffling," "fast forced evolution," or "molecular breeding," have been described by the present inventors and co-workers in the publications, patents and patent applications noted above.

In one class of embodiments, the recombination procedure starts with at least two substrates that generally show substantial sequence identity to each other (i.e., at least about 30%, 50%, 70%, 80% or 90% sequence identity), but differ from each other at certain positions. The difference can be any type of mutation, for example, substitutions, insertions and deletions. Often, different segments differ from each other in about 5–20 positions. For recombination to generate increased diversity relative to the starting materials, the starting materials must differ from each other in at least two nucleotide positions. That is, if there are only two substrates, there should be at least two divergent positions. If there are three substrates, for example, one substrate can differ from the second at a single position, and the second can differ from the third at a different single position. The starting DNA segments can be natural variants of each other, for example, allelic or species variants. The segments can also be from nonallelic genes showing some degree of structural and usually functional relatedness (e.g., different genes within a superfamily, such as the cytochrome P450 super family). The starting DNA segments can also be induced variants of each other. For example, one DNA segment can be produced by error-prone PCR replication of the other, or by substitution of a mutagenic cassette. Induced mutants can also be prepared by propagating one (or both) of the segments in a mutagenic strain. In these situations, strictly speaking, the second DNA segment is not a single segment but a large family of related segments. The different segments forming the starting materials are often the same length or substantially the same length. However, this need not be the case; for example; one segment can be a subsequence of another. The segments can be present as part of larger molecules, such as vectors, or can be in isolated form.

The starting DNA segments are recombined by any of the sequence recombination formats provided herein to generate a diverse library of recombinant DNA segments. Such a library can vary widely in size from having fewer than 10 to more than $10^5$, $10^9$, $10^{12}$ or more members. In some embodiments, the starting segments and the recombinant libraries generated will include full-length coding sequences and any essential regulatory sequences, such as a promoter and polyadenylation sequence, required for expression. In other embodiments, the recombinant DNA segments in the library can be inserted into a common vector providing sequences necessary for expression before performing screening/selection.

Use of Restriction Enzyme Sites to Recombine Mutations

In some situations it is advantageous to use restriction enzyme sites in nucleic acids to direct the recombination of mutations in a nucleic acid sequence of interest. These techniques are particularly preferred in the evolution of fragments that cannot readily be shuffled by existing methods due to the presence of repeated DNA or other problematic primary sequence motifs. These situations also include recombination formats in which it is preferred to retain certain sequences unmutated. The use of restriction enzyme sites is also preferred for shuffling large fragments (typically greater than 10 kb), such as gene clusters that cannot be readily shuffled and "PCR-amplified" because of their size. Although fragments up to 50 kb have been reported to be amplified by PCR (Barnes, *Proc. Natl. Acad. Sci. U.S.A.* 91:2216–2220 (1994)), it can be problematic for fragments over 10 kb, and thus alternative methods for shuffling in the range of 10–50 kb and beyond are preferred. Preferably, the restriction endonucleases used are of the Class II type (Sambrook, Ausubel and Berger, supra) and of these, preferably those which generate nonpalindromic sticky end overhangs such as Alwn I, Sfi I or BstX1. These enzymes generate nonpalindromic ends that allow for efficient ordered reassembly with DNA ligase. Typically, restriction enzyme (or endonuclease) sites are identified by conventional restriction enzyme mapping techniques (Sambrook, Ausubel, and Berger, supra.), by analysis of sequence information for that gene, or by introduction of desired restriction sites into a nucleic acid sequence by synthesis (i.e. by incorporation of silent mutations).

The DNA substrate molecules to be digested can either be from in vivo replicated DNA, such as a plasmid preparation, or from PCR amplified nucleic acid fragments harboring the restriction enzyme recognition sites of interest, preferably near the ends of the fragment. Typically, at least two variants of a gene of interest, each having one or more mutations, are digested with at least one restriction enzyme determined to cut within the nucleic acid sequence of interest. The restriction fragments are then joined with DNA ligase to generate full length genes having shuffled regions. The number of regions shuffled will depend on the number of cuts within the nucleic acid sequence of interest. The shuffled molecules can be introduced into cells as described above and screened or selected for a desired property as described herein. Nucleic acid can then be isolated from pools (libraries), or clones having desired properties and subjected to the same procedure until a desired degree of improvement is obtained.

In some embodiments, at least one DNA substrate molecule or fragment thereof is isolated and subjected to mutagenesis. In some embodiments, the pool or library of religated restriction fragments are subjected to mutagenesis before the digestion-ligation process is repeated. "Mutagenesis" as used herein comprises such techniques known in the art as PCR mutagenesis, oligonucleotide-directed mutagenesis, site-directed mutagenesis, etc., and recursive sequence recombination by any of the techniques described herein.

Reassembly PCR

A further technique for recombining mutations in a nucleic acid sequence utilizes "reassembly PCR." This method can be used to assemble multiple segments that have been separately evolved into a full length nucleic acid template such as a gene. This technique is performed when a pool of advantageous mutants is known from previous work or has been identified by screening mutants that may have been created by any mutagenesis technique known in the art, such as PCR mutagenesis, cassette mutagenesis, doped oligo mutagenesis, chemical mutagenesis, or propagation of the DNA template in vivo in mutator strains. Boundaries defining segments of a nucleic acid sequence of interest preferably lie in intergenic regions, introns, or areas of a gene not likely to have mutations of interest. Preferably, oligonucleotide primers (oligos) are synthesized for PCR amplification of segments of the nucleic acid sequence of interest, such that the sequences of the oligonucleotides overlap the junctions of two segments. The overlap region is typically about 10 to 100 nucleotides in length. Each of the segments is amplified with a set of such primers. The PCR products are then "reassembled" according to assembly protocols such as those discussed herein to assemble randomly fragmented genes. In brief, in an assembly protocol the PCR products are first purified away from the primers, by, for example, gel electrophoresis or size exclusion chromatography. Purified products are mixed together and subjected to about 1–10 cycles of denaturing, reannealing, and extension in the presence of polymerase and deoxynucleoside triphosphates (dNTP's) and appropriate buffer salts in the absence of additional primers ("self-priming"). Subsequent PCR with primers flanking the gene are used to amplify the yield of the fully reassembled and shuffled genes.

In some embodiments, the resulting reassembled genes are subjected to mutagenesis before the process is repeated.

In a further embodiment, the PCR primers for amplification of segments of the nucleic acid sequence of interest are used to introduce variation into the gene of interest as follows. Mutations at sites of interest in a nucleic acid sequence are identified by screening or selection, by sequencing homologues of the nucleic acid sequence, and so on. Oligonucleotide PCR primers are then synthesized which encode wild type or mutant information at sites of interest. These primers are then used in PCR mutagenesis to generate libraries of full length genes encoding permutations of wild type and mutant information at the designated positions. This technique is typically advantageous in cases where the screening or selection process is expensive, cumbersome, or impractical relative to the cost of sequencing the genes of mutants of interest and synthesizing mutagenic oligonucleotides.

Oligonucleotide and in silico shuffling formats for Mycotoxin Detoxification Shuffling Two additional related formats are useful in the practice of the present invention. The first, referred to as "in silico" shuffling utilizes computer algorithms to perform "virtual" shuffling using genetic operators in a computer. As applied to the present invention, mycotoxin detoxification nucleic acid sequence strings are recombined in a computer system and desirable products are made, e.g., by reassembly PCR or ligation of synthetic oligonucleotides, or other available techniques. In silico shuffling is described in detail in Selifonov and Stemmer in "METHODS FOR MAKING CHARACTER STRINGS, POLYNUCLEOTIDES & POLYPEPTIDES HAVING DESIRED CHARACTERISTICS" filed Feb. 05, 1999, U.S. Ser. No. 60/118854. In brief, genetic operators (algorithms which represent given genetic events such as point mutations, recombination of two strands of homologous nucleic acids, etc.) are used to model recombinational or mutational events which can occur in one or more nucleic acid, e.g., by aligning nucleic acid sequence strings (using standard alignment software, or by manual inspection and alignment) and predicting recombinational outcomes based upon selected genetic algorithms (mutation, recombination, etc.). The predicted recombinational outcomes are used to produce corresponding molecules, e.g., by oligonucleotide synthesis and reassembly PCR. As applied to the present invention, mycotoxin detoxification nucleic acids are aligned and recombined in silico, using any desired genetic operator, to produce mycotoxin detoxification character strings which are then generated synthetically for subsequent screening.

The second useful format is referred to as "oligonucleotide mediated shuffling" in which oligonucleotides corresponding to a family of related homologous nucleic acids (e.g., as applied to the present invention, families of homologous mycotoxin detoxification variants of a nucleic acid) which are recombined to produce selectable nucleic acids.

This format is described in detail in Crameri et al. "OLIGONUCLEOTIDE MEDIATED NUCLEIC ACID RECOMBINATION" filed Feb. 5, 1999, U.S. Ser. No. 60/118,813 and Crameri et al. "OLIGONUCLEOTIDE MEDIATED NUCLEIC ACID RECOMBINATION" filed Jun. 24, 1999, U.S. Ser. No. 60/141,049. In brief, selected oligonucleotides corresponding to multiple homologous parental nucleic acids are synthesized, ligated and elongated (typically in a recursive format), typically either in a polymerase or ligase-mediated elongation reaction, to produce full-length mycotoxin detoxification nucleic acids. The technique can be used to recombine homologous or even non-homologous mycoltoxin detoxification nucleic acid sequences.

One advantage of oligonucleotide-mediated recombination is the ability to recombine homologous nucleic acids with low sequence similarity, or even non-homologous nucleic acids. In these low-homology oligonucleotide shuffling methods, one or more set of fragmented nucleic acids (e.g., oligonucleotides corresponding to multiple mycotoxin detoxification nucleic acids) are recombined, e.g., with a with a set of crossover family diversity oligonucleotides. Each of these crossover oligonucleotides have a plurality of sequence diversity domains corresponding to a plurality of sequence diversity domains from homologous or non-homologous nucleic acids with low sequence similarity. The fragmented oligonucleotides, which are derived by comparison to one or more homologous or non-homologous nucleic acids, can hybridize to one or more region of the crossover oligos, facilitating recombination.

When recombining homologous nucleic acids, sets of overlapping family gene shuffling oligonucleotides (which are derived by comparison of homologous nucleic acids, by synthesis of corresponding oligonucleotides) are hybridized and elongated (e.g., by reassembly PCR or ligation), providing a population of recombined nucleic acids, which can be selected for a desired trait or property. The set of overlapping family shuffling gene oligonucleotides includes a plurality of oligonucleotide member types which have consensus region subsequences derived from a plurality of homologous target nucleic acids.

Typically, as applied to the present invention, family gene shuffling oligonucleotide which include one or more mycotoxin detoxification nucleic acid(s) are provided by aligning homologous nucleic acid sequences to select conserved regions of sequence identity and regions of sequence diversity. A plurality of family gene shuffling oligonucleotides are synthesized (serially or in parallel) which correspond to at least one region of sequence diversity.

Sets of fragments, or subsets of fragments used in oligonucleotide shuffling approaches can be provided by cleaving one or more homologous nucleic acids (e.g., with a DNase), or, more commonly, by synthesizing a set of oligonucleotides corresponding to a plurality of regions of at least one nucleic acid (typically oligonucleotides corresponding to a full-length nucleic acid are provided as members of a set of nucleic acid fragments). In the shuffling procedures herein, these cleavage fragments can be used in conjunction with family gene shuffling oligonucleotides, e.g., in one or more recombination reaction to produce recombinant rnycotoxin detoxification nucleic acid(s).

One final synthetic variant worth noting is found in "SHUFFLING OF CODON ALTERED GENES" by Patten et al. filed Sep. 29, 1998, (U.S. Ser. No. 60/102,362), Jan. 29, 1999 (U.S. Ser. No. 60/117,729), and Sep. 28, 1999, U.S. Ser. No. 09/407,800. As noted in detail in this set of related applications, one way of generating diversity in a set of nucleic acids to be shuffled (i.e., as applied to the present invention, mycotoxin detoxification nucleic acids), is to provide codon-altered nucleic acids which can be shuffled to provide access to sequence space not present in naturally occurring sequences. In brief, by synthesizing nucleic acids in which the codons which encode polypeptides are altered, it is possible to access a completely different mutational spectrum upon subsequent mutation of the nucleic acid. This increases the sequence diversity of the starting nucleic acids for shuffling protocols, which alters the rate and results of forced evolution procedures. Codon modification procedures can be used to modify any mycotoxin detoxification nucleic acid herein, e.g., prior to performing DNA shuffling.

In brief, oligonucleotide sets comprising codon variations are synthesized and reassembled into full-length nucleic acids. The oligonucleotide sets can themselves be shuffled (e.g., where the oligonucleotides to be reassembled provide sequence diversity at selected sites), and/or the full-length sequences can be shuffled by any available procedure to produce diverse sets of mycotoxin detoxification nucleic acids.

Site Directed Mutagenesis (SDM) with Oligonucleotides Encoding Homologue Mutations Followed by Shuffling In some embodiments of the invention, sequence information from one or more substrate sequences is added to a given "parental" sequence of interest, with subsequent recombination between rounds of screening or selection. Typically, this is done with site-directed mutagenesis performed by techniques well known in the art (e.g., Berger, Ausubel and Sambrook, supra.), or by the oligonucleotide or in silico methods noted above, with one substrate as template and oligonucleotides encoding single or multiple mutations from other substrate sequences, e.g. homologous genes. After screening or selection for an improved phenotype of interest, the selected recombinant(s) can be further evolved, using RSR techniques described herein. After screening or selection, site-directed mutagenesis can be done again with another collection of oligonucleotides encoding homologue mutations, and the above process repeated until the desired properties are obtained.

When the difference between two homologues is one or more single point mutations in a codon, degenerate oligonucleotides can be used that encode the sequences in both homologues. One oligonucleotide can include many such degenerate codons and still allow one to exhaustively search all permutations over that block of sequence.

When the homologue sequence space is very large, it can be advantageous to restrict the search to certain variants. Thus, for example, computer modeling tools (Lathrop et al. (1996) *J. Mol. Biol.,* 255: 641–665) can be used to model each homologue mutation onto the target protein and discard any mutations that are predicted to grossly disrupt structure and function.

In Vitro DNA Shuffling Formats

In one embodiment for shuffling DNA sequences in vitro, the initial substrates for recombination are a pool of related sequences, e.g., different variant forms, as homologs from different individuals, strains, or species of an organism, or related sequences from the same organism, as allelic variations. The sequences can be DNA or RNA and can be of various lengths depending on the size of the gene or DNA fragment to be recombined or reassembled. Preferably the sequences are from 40 base pairs (bp) to 50 kilobases (kb).

The pool of related substrates are converted into overlapping fragments, e.g., from about 5 bp to 5 kb or more. Often, for example, the size of the fragments is from about 10 bp to 1000 bp, e.g., about 30 or 40 bp to about 100 bp, e.g., about 100 bp to 500 bp. The conversion can be effected by a number of different methods, such as DNase I or RNase digestion, random shearing, partial restriction enzyme digestion or oligonucleotide synthesis. For discussions of protocols for the isolation, manipulation, enzymatic digestion, and the like of nucleic acids, see, for example, Sambrook et al. and Ausubel, both supra. The concentration of nucleic acid fragments of a particular length and sequence is often less than 0.1% or 1% by weight of the total nucleic acid. The number of different specific nucleic acid fragments in the mixture is usually at least about 100, 500 or 1000.

The mixed population of nucleic acid fragments are converted to at least partially single-stranded form using a variety of techniques, including, for example, heating, chemical denaturation, use of DNA binding proteins, and the like. Conversion can be effected by heating to about 80° C. to 100° C., more preferably from 90° C. to 96° C., to form single-stranded nucleic acid fragments and then reannealing. Conversion can also be effected by treatment with single-stranded DNA binding protein (see Wold (1997) *Annu. Rev. Biochem.* 66:61–92) or recA protein (see, e.g., Kiianitsa (1997) *Proc. Natl. Acad. Sci. USA* 94:7837–7840). Single-stranded nucleic acid fragments having regions of sequence identity with other single-stranded nucleic acid fragments can then be reannealed by cooling to 20° C. to 75° C., and preferably from 40° C. to 65° C. Renaturation can be accelerated by the addition of polyethylene glycol (PEG), other volume-excluding reagents or salt. The salt concentration is preferably from 0 mM to 200 mM, more preferably the salt concentration is from 10 mM to 100 mM. The salt may be KCl or NaCl. The concentration of PEG is preferably from 0% to 20%, more preferably from 5% to 10%. The fragments that reanneal can be from different substrates. The annealed nucleic acid fragments are incubated in the presence of a nucleic acid polymerase, such as Taq or Klenow, and dNTP's (i.e. DATP, dCTP, dGTP and dTTP). If regions of sequence identity are large, Taq polymerase can be used with an annealing temperature of between 45–65° C. If the areas of identity are small, Klenow polymerase can be used with an annealing temperature of between 20–30° C. The polymerase can be added to the random nucleic acid fragments prior to annealing, simultaneously with annealing or after annealing.

The process of denaturation, renaturation and incubation in the presence of polymerase of overlapping fragments to generate a collection of polynucleotides containing different permutations of fragments is sometimes referred to as shuffling of the nucleic acid in vitro. This cycle is optionally repeated for a desired number of times. Preferably the cycle is repeated from 2 to 100 times, more preferably the sequence is repeated from 10 to 40 times. The resulting nucleic acids are a selectable family of double-stranded polynucleotides of from about 50 bp to about 100 kb, preferably from 500 bp to 50 kb. The population represents variants of the starting substrates showing substantial sequence identity thereto but also diverging at several positions. The population has many more members than the starting substrates. The population of fragments resulting from shuffling is used to transform host cells, optionally after cloning into a vector.

In one embodiment utilizing in vitro shuffling, subsequences of recombination substrates can be generated by amplifying the full-length sequences under conditions which produce a substantial fraction, typically at least 20 percent or more, of incompletely extended amplification products. Another embodiment uses random primers to prime the entire template DNA to generate less than full length amplification products. The amplification products, including the incompletely extended amplification products are denatured and subjected to at least one additional cycle of reannealing and amplification. This variation, in which at least one cycle of reannealing and amplification provides a substantial fraction of incompletely extended products, is termed "stuttering." In the subsequent amplification round, the partially extended (less than full length) products reanneal to and prime extension on different sequence-related template species. In another embodiment, the conversion of substrates to fragments can be effected by partial PCR amplification of substrates.

In another embodiment, a mixture of fragments is spiked with one or more oligonucleotides. The oligonucleotides can be designed to include precharacterized mutations of a wildtype sequence, or sites of natural variations between individuals or species. The oligonucleotides also include sufficient sequence or structural homology flanking such mutations or variations to allow annealing with the wildtype fragments. Annealing temperatures can be adjusted depending on the length of homology.

In a further embodiment, recombination occurs in at least one cycle by template switching, such as when a DNA fragment derived from one template primes on the homologous position of a related but different template. Template switching can be induced by addition of recA (see, Kiianitsa (1997) supra), rad51 (see, Namsaraev (1997) *Mol. Cell. Biol.* 17:5359–5368), rad55 (see, Clever (1997) *EMBO J.* 16:2535–2544), rad57 (see, Sung (1997) *Genes Dev.* 11: 1111–1121) or other polymerases (e.g., viral polymerases, reverse transcriptase) to the amplification mixture. Template switching can also be increased by increasing the DNA template concentration.

Another embodiment utilizes at least one cycle of amplification, which can be conducted using a collection of overlapping single-stranded DNA fragments of related sequence, and different lengths. Fragments can be prepared using a single stranded DNA phage, such as M13 (see, Wang (1997) *Biochemistry* 36:9486–9492). Each fragment can hybridize to and prime polynucleotide chain extension of a second fragment from the collection, thus forming sequence-recombined polynucleotides. In a further variation, ssDNA fragments of variable length can be generated from a single primer by Pfu, Taq, Vent, Deep Vent, UlTma DNA polymerase or other DNA polymerases on a first DNA template (see, Cline (1996) *Nucleic Acids Res.* 24:3546–3551). The single stranded DNA fragments are used as primers for a second, Kunkel-type template, consisting of a uracil-containing circular ssDNA. This results in multiple substitutions of the first template into the second. See, Levichkin (1995) *Mol. Biology* 29:572–577; Jung (1992) *Gene* 121:17–24.

In some embodiments of the invention, shuffled nucleic acids obtained by use of the recursive recombination methods of the invention, are put into a cell and/or organism for screening. Shuffled monooxygenase genes can be introduced into, for example, bacterial cells, yeast cells, fungal cells vertebrate cells, invertebrate cells or plant cells for initial screening. Bacillus species (such as *B. subtilis* and *E. coli* are two examples of suitable bacterial cells into which one can insert and express shuffled monooxygenase genes which provide for convenient shuttling to other cell types (a variety of vectors for shuttling material between these bacterial cells and eukaryotic cells are available; see, Sambrook, Ausubel and Berger, all supra). The shuffled genes can be introduced into bacterial, fungal or yeast cells either by integration into the chromosomal DNA or as plasmids.

Although bacterial and yeast systems are most preferred in the present invention, in one embodiment, shuffled genes can also be introduced into plant cells for production purposes (it will be appreciated that transgenic plants are, increasingly, an important source of industrial enzymes). Thus, a transgene of interest can be modified using the recursive sequence recombination methods of the invention in vitro and reinserted into the cell for in vivolin situ selection for the new or improved monooxygenase property, in bacteria, eukaryotic cells, or whole eukaryotic organisms.

In vivo DNA Shuffling Formats

In some embodiments of the invention, DNA substrate molecules are introduced into cells, wherein the cellular machinery directs their recombination. For example, a library of mutants is constructed and screened or selected for mutants with improved phenotypes by any of the techniques described herein. The DNA substrate molecules encoding the best candidates are recovered by any of the techniques described herein, then fragmented and used to transfect a plant host and screened or selected for improved function. If further improvement is desired, the DNA substrate molecules are recovered from the host cell, such as by PCR, and the process is repeated until a desired level of improvement is obtained. In some embodiments, the fragments are denatured and reannealed prior to transfection, coated with recombination stimulating proteins such as recA, or co-transfected with a selectable marker such as $Neo^R$ to allow the positive selection for cells receiving recombined versions of the gene of interest. Methods for in vivo shuffling are described in, for example, PCT application WO 98/13487 and WO 97/20078.

The efficiency of in vivo shuffling can be enhanced by increasing the copy number of a gene of interest in the host cells. For example, the majority of bacterial cells in stationary phase cultures grown in rich media contain two, four or eight genomes. In minimal medium the cells contain one or two genomes. The number of genomes per bacterial cell thus depends on the growth rate of the cell as it enters stationary phase. This is because rapidly growing cells contain multiple replication forks, resulting in several genomes in the cells after termination. The number of genomes is strain dependent, although all strains tested have more than one chromosome in stationary phase. The number of genomes in stationary phase cells decreases with time. This appears to be due to fragmentation and degradation of entire chromosomes, similar to apoptosis in mammalian cells. This fragmentation of genomes in cells containing multiple genome copies results in massive recombination and mutagenesis. The presence of multiple genome copies in such cells results in a higher frequency of homologous recombination in these cells, both between copies of a gene in different genomes within the cell, and between a genome within the cell and a transfected fragment. The increased frequency of recombination allows one to evolve a gene evolved more quickly to acquire optimized characteristics.

In nature, the existence of multiple genomic copies in a cell type would usually not be advantageous due to the greater nutritional requirements needed to maintain this copy number. However, artificial conditions can be devised to select for high copy number. Modified cells having recombinant genomes are grown in rich media (in which conditions, multicopy number should not be a disadvantage) and exposed to a mutagen, such as ultraviolet or gamma irradiation or a chemical mutagen, e.g., mitomycin, nitrous acid, photoactivated psoralens, alone or in combination, which induces DNA breaks amenable to repair by recombination. These conditions select for cells having multicopy number due to the greater efficiency with which mutations can be excised. Modified cells surviving exposure to mutagen are enriched for cells with multiple genome copies. If desired, selected cells can be individually analyzed for genome copy number (e.g., by quantitative hybridization with appropriate controls). For example, individual cells can be sorted using a cell sorter for those cells containing more DNA, e.g., using DNA specific fluorescent compounds or sorting for increased size using light dispersion. Some or all of the collection of cells surviving selection are tested for the presence of a gene that is optimized for the desired property.

In one embodiment, phage libraries are made and recombined in mutator strains such as cells with mutant or imparied gene products of mutS, mutT, mutH, mutL, ovrD, dcm, vsr, umuC, umuD, sbcB, recJ, etc. The impairment is achieved by genetic mutation, allelic replacement, selective inhibition by an added reagent such as a small compound or an expressed antisense RNA, or other techniques. High multiplicity of infection (MOI) libraries are used to infect the cells to increase recombination frequency.

Additional strategies for making phage libraries and or for recombining DNA from donor and recipient cells are set forth in U.S. Pat. No. 5,521,077. Additional recombination strategies for recombining plasmids in yeast are set forth in WO 97 07205.

Recursive macroshuffling techniques are described in U.S. Pat. 5,811,238 to Stemmer.

Whole Genome Shuffling

In one embodiment, the selection methods herein are utilized in a "whole genome shuffling" format. An extensive guide to the many forms of whole genome shuffling is found in the pioneering application to the inventors and their co-workers entitled "Evolution of Whole Cells and Organisms by Recursive Sequence Recombination," by del Cardyre et al. e.g., WO98/31837, PCT/US99/15972, and Ser. No. 09/354,922.

In brief, whole genome shuffling makes no presuppositions at all regarding what nucleic acids may confer a desired property. Instead, entire genomes (e.g., from a genomic library, or isolated from an organism) are shuffled in cells and selection protocols applied to the cells. Thus, as applied to the present invention, cell genomes or sub genomes (e.g., libraries) are recombined and resulting recombinant cells comprising the recombined nucleic acids are selected for mycotoxin detoxification activity. Thus, one feature of the invention is a cell (e.g., plant, animal, bacterial, or even fungal cell which comprises mycotoxin detoxification activity). These cells can be used to produce anti-mycotoxin extracts or can be applied to reduce fungal growth and/or pathogenicity in a system of interest.

Use of RecA

The frequency of recombination between nucleic acids in the mycotoxin detoxification shuffling procedures herein can be increased by coating the nucleic acids with a recombinogenic protein, e.g., before or after introduction into cells. See Pati et al., *Molecular Biology of Cancer* 1, 1 (1996); Sena & Zarling, *Nature Genetics* 3, 365 (1996); Revet et al., *J. Mol. Biol.* 232, 779–791 (1993); Kowalczkowski & Zarling in *Gene Targeting* (CRC 1995), Ch. 7. The recombinogenic protein promotes homologous pairing and/or strand exchange. The best characterized recA protein is from *E. coli* and is available from Pharmacia (Piscataway, N.J.). In addition to the wild-type protein, a number of mutant recA-like proteins have been identified (e.g., recA803). Further, many organisms have recA-like recombinases with strand-transfer activities (e.g., Ogawa et al., *Cold Spring Harbor Symposium on Quantitative Biology* 18, 567–576

(1993); Johnson & Symington, *Mol. Cell. Biol.* 15, 4843–4850 (1995); Fugisawa et al., *Nucl. Acids Res.* 13, 7473 (1985); Hsieh et al., *Cell* 44, 885 (1986); Hsieh et al., *J. Biol. Chem.* 264, 5089 (1989); Fishel et al., *Proc. Natl. Acad. Sci. USA* 85, 3683 (1988); Cassuto et al., *Mol. Gen. Genet.* 208, 10 (1987); Ganea et al., *Mol. Cell Biol.* 7, 3124 (1987); Moore et al., *J. Biol. Chem.* 19, 11108 (1990); Keene et al., *Nucl. Acids Res.* 12, 3057 (1984); Kimiec, *Cold Spring Harbor Symp.* 48, 675 (1984); Kimeic, *Cell* 44, 545 (1986); Kolodner et al., *Proc. Natl. Acad. Sci. USA* 84, 5560 (1987); Sugino et al., *Proc. Nati. Acad. Sci. USA* 85, 3683 (1985); Halbrook et al., *J. Biol. Chem.* 264, 21403 (1989); Eisen et al., *Proc. Natl. Acad. Sci. USA* 85, 7481 (1988); McCarthy et al., *Proc. Natl. Acad. Sci. USA* 85, 5854 (1988); Lowenhaupt et al., *J. Biol. Chem.* 264, 20568 (1989). Examples of such recombinase proteins include recA, recA803, uvsX, (Roca, A. I., *Crit. Rev. Biochem. Molec. Biol.* 25, 415 (1990)), sep1 (Kolodner et al., *Proc. Natl. Acad. Sci. (U.S.A.)* 84, 5560 (1987); Tishkoff et al., *Molec. Cell. Biol.* 11, 2593), RuvC (Dunderdale et al., *Nature* 354, 506 (1991)), DST2, KEM1, XRN1 (Dykstra et al., *Molec. Cell. Biol.* 11, 2583 (1991)), STPα/DST1 (Clark et al., *Molec. Cell. Biol.* 11, 2576 (1991)), HPP-1 (Moore et al., *Proc. Natl. Acad. Sci. (U.S.A.)* 88, 9067 (1991)), other eukaryotic recombinases (Bishop et al., *Cell* 69, 439 (1992); Shinohara et al., *Cell* 69, 457. RecA protein forms a nucleoprotein filament when it coats a single-stranded DNA. In this nucleoprotein filament, one monomer of recA protein is bound to about 3 nucleotides. This property of recA to coat single-stranded DNA is essentially sequence independent, although particular sequences favor initial loading of recA onto a polynucleotide (e.g., nucleation sequences). The nucleoprotein filament(s) can be formed on essentially any DNA to be shuffled and can form complexes with both single-stranded and double-stranded DNA in procaryotic and eukaryotic cells. RecA mediated techniques are also found in WO/93/22443.

Before contacting with recA or other recombinase, mycotoxin detoxification fragments are optionally denatured, e.g., by heat-treatment. RecA protein is then added at a concentration of about 1–10 μM. After incubation, the recA-coated single-stranded DNA is introduced into recipient cells by conventional methods, such as chemical. transformation or electroporation. In whole cell shuffling techniques, the fragments undergo homologous recombination with cognate endogenous genes. Because of the increased frequency of recombination due to recombinase coating, the fragments need not be introduced as components of vectors.

Fragments are sometimes coated with other nucleic acid binding proteins that promote recombination, protect nucleic acids from degradation, or target nucleic acids to the nucleus. Examples of such proteins includes Agrobacterium virE2 (Durrenberger et al., *Proc. Natl. Acad. Sci. USA* 86, 9154–9158 (1989)). Alternatively, recipient strains can be deficient in RecD activity. Single stranded ends can also be generated by 3'–5' exonuclease activity or restriction enzymes producing 5' overhangs.

Transducing Shuffled Nucleic Acids into Plants

As noted herein, it is particularly desirable to transduce plants with shuffled nucleic acids to reduce the level of mycotoxins in the plants, and/or to practice the shuffling procedures in plant cells. Reduction of mycotoxins benefits the plants by making them resistant to mycotoxicosis, as well as be making the plants safer for consumption.

Methods of transducing plant cells with nucleic acids are generally available. In addition to Berger, Ausubel and Sambrook, useful general references for plant cell cloning, culture and regeneration include Jones (ed) (1995) *Plant Gene Transfer and Expression Protocols—Methods in Molecular Biology, Volume* 49 Human Press Towata N.J.; Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of Cell culture media are described in Atlas and Parks (eds) The Handbook of Microbiological Media (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS). Additional details regarding plant cell culture are found in R. R. D. Croy, Ed. *Plant Molecular Biolgy* (1993) Bios Scientific Publishers, Oxford, U.K.

The nucleic acid constructs of the invention are introduced into plant cells, either in culture or in the organs of a plant by a variety of conventional techniques. For example, the DNA construct can be introduced directly into the genomic DNA of the plant cell using techniques such as electroporation and microinjection of plant cell protoplasts, or the DNA constructs can be introduced directly to plant cells using ballistic methods, such as DNA particle bombardment. Alternatively, the DNA constructs are combined with suitable T-DNA flanking regions and introduced into a conventional *Agrobacterium tumefaciens* host vector. The virulence functions of the *Agrobacterium tumefaciens* host directs the insertion of the construct and adjacent marker into the plant cell DNA when the cell is infected by the bacteria.

Microinjection techniques are known in the art and well described in the scientific and patent literature. For example, a number of methods are described in Jones (ed) (1995) *Plant Gene Transfer and Expression Protocols—Methods in Molecular Biology, Volume* 49 Human Press Towata N.J., as well as in the other references noted herein and available in the literature.

For example, the introduction of DNA constructs using polyethylene glycol precipitation is described in Paszkowski, et al., *EMBO J.* 3:2717 (1984). Electroporation techniques are described in Fromm, et al., *Proc. Nat'l. Acad. Sci. USA* 82:5824 (1985). Ballistic transformation techniques are described in Klein, et al., *Nature* 327:70–73 (1987). Additional details are found in Jones (1995) supra.

i Agrobacterium tumefaciens-mediated transformation techniques, including disarming and use of binary vectors, are also well described in the scientific literature. See, for example Horsch, et al., *Science* 233:496–498 (1984), and Fraley, et al., *Proc. Nat'l. Acad. Sci. USA* 80:4803 (1983). Agrobacterium-mediated transformation is a preferred method of transformation of both monocots and particularly dicots.

To use shuffled sequences, recombinant DNA vectors suitable for transformation of plant cells are prepared. A DNA sequence coding for the desired shuffled mycotoxin detoxification DNA is transduced into the plant. Where the sequence is expressed, the sequence is optionally combined with transcriptional and translational initiation regulatory sequences which further direct the transcription or translation of the sequence from shuffled the gene in the intended tissues of the transformed plant.

Regeneration of Transgenic Plants

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., *Protoplasts Isolation and Culture, Handbook of Plant Cell Culture*, pp. 124–176, Macmillian Publishing Company, New York, (1983); and Binding, *Regeneration of Plants, Plant Protoplasts*, pp. 21–73, CRC Press, Boca Raton, (1985). Regeneration can also be obtained from plant callus, explants, somatic embryos (Dandekar, et al., *J. Tissue Cult. Meth.* 12:145 (1989); McGranahan, et al., *Plant Cell Rep.* 8:512 (1990)), organs, or parts thereof. Such regeneration techniques are described generally in Klee, et al., *Ann. Rev. of Plant Phys.* 38:467–486 (1987). Additional details are found in Payne (1992) and Jones (1995), both supra.

Preferred plants for expression of mycotoxin resistance genes include those for which mycotoxins are a significant problem, such as plants in the family Graminae (including corn, rye, triticale, barley, millet, rice, wheat, oats, etc.) plants in the family Leguminosa (e.g., peanuts, peas, beans, and the like) and nut plants (walnut, pecan, etc.) .

More generally, important commercial crops which benefit from mycotoxin detoxification include both monocots and dicots. Monocots such as plants in the grass family (Gramineae), such as plants in the sub families Fetucoideae and Poacoideae, which together include several hundred genera including plants in the genera Agrostis, Phleum, Dactylis, Sorgum, Setaria, Zea (e.g., corn), Oryza (e.g., rice), Triticum (e.g., wheat), Secale (e.g., rye), Avena (e.g., oats), Hordeum (e.g., barley), Saccharum, Poa, Festuca, Stenotaphrum, Cynodon, Coix, the Olyreae, Phareae and many others. As noted, plants in the family Gramineae are a particularly preferred target plants for the methods of the invention.

Additional preferred targets include other commercially important crops, e.g., from the families Compositae (the largest family of vascular plants, including at least 1,000 genera, including important commercial crops such as sunflower), and Leguminosae or the "pea family," which includes several hundred genera, including many commercially valuable crops such as pea, beans, lentil, peanut, yam bean, cowpeas, velvet beans, soybean, clover, alfalfa, lupine, vetch, lotus, sweet clover, wisteria, and sweetpea.

Plants in the genera Fragaria, Lotus, Medicago, Onobrychis, Trifolium, Trigonella, Vigna, Citrus, Linum, Geranium, Manihot, Daucus, Brassica, Raphanus, Sinapis, Atropa, Capsicum, Datura, Hyoscyamus, Lycopersicon, Nicotiana, Solonum, Petunia, Digitalis, Majorana, Cichorium, Helianthus, Lactuca, Bromus, Asparagus, Antirrhinum, Heterocallis, Nemesia, Pelargonium, Panicum, Pennisetum, Ranunculus, Senecio, Salpiglossis, Cucumis, Browaalia, Glycine, Lolium, Zea, Triticum, Sorghum, Malus, and Apium are targets for mycotoxin detoxification, as are plants in the genera Agrostis, Phleum, Dactylis, Sorgum, Setaria, Zea, Oryza, Triticum, Secale, Avena, Hordeum, Saccharum, Poa, Festuca, Stenotaphrum, Cynodon, Coix, Olyreae, Phareae, Glycine, Pisum, Cicer, Phaseolus, Lens, and Arachis are targets for acquiring mycotoxin detoxification activity.

Common crop plants which are targets for mycotoxin detoxification include corn, rice, triticale, rye, cotton, soybean, sorghum, wheat, oats, barley, millet, sunflower, canola, peas, beans, lentils, peanuts, yam beans, cowpeas, velvet beans, clover, alfalfa, lupine, vetch, lotus, sweet clover, wisteria, sweetpea and nut plants (e.g., walnut, pecan, etc).

In construction of recombinant expression cassettes of the invention, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumafaciens,* and other transcription initiation regions from various plant genes known to those of skill. Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers.

Any of a number of promoters which direct transcription in plant cells can be suitable. The promoter can be either constitutive or inducible. In addition to the promoters noted above, promoters of bacterial origin which operate in plants include the octopine synthase promoter, the nopaline synthase promoter and other promoters derived from native Ti plasmids. See, Herrara-Estrella et al. (1983), *Nature, 303:209–213.* Viral promoters include the 35S and 19S RNA promoters of cauliflower mosaic virus. See, Odell et al. (1985) *Nature, 313:810–812.* Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer, (1988) *EMBO J. 7:3315–3327.* Many other promoters are in current use and can be coupled to a mycotoxin detoxification nucleic acid to direct expression of the nucleic acid.

If polypeptide expression is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products of the invention will typically comprise a nucleic acid subsequence which confers a selectable phenotype on plant cells. The vector comprising the sequence will typically comprise a marker gene which confers a selectable phenotype on plant cells. For example, the marker may encode biocide tolerance, particularly antibiotic tolerance, such as tolerance to kanamycin, G418, bleomycin, hygromycin, or herbicide tolerance, such as tolerance to chlorosluforon, or phosphinothricin (the active ingredient in the herbicides bialaphos and Basta). For example, crop selectivity to specific herbicides can be conferred by engineering genes into crops which encode appropriate herbicide metabolizing enzymes from other organisms, such as microbes. See, Padgette et al. (1996) "New weed control opportunities: Development of soybeans with a Round UP Ready™ gene" In: *Herbicide-Resistant Crops* (Duke, ed.), pp 53–84, CRC Lewis Publishers, Boca Raton ("Padgette, 1996"); and Vasil (1996) "Phosphinothricin-resistant crops" In: *Herbicide-Resistant Crops* (Duke, ed.), pp 85–91, CRC Lewis Publishers, Boca Raton) (Vasil, 1996).

Transgenic plants have been engineered to express a variety of herbicide tolerance/metabolizing genes, from a variety of organisms—and the expression of these genes in concert with the mycotoxin detoxification nucleic acid can be used a selectable marker for the presence of a vector comprising the mycotoxin detoxification nucleic acid. For example, acetohydroxy acid synthase, which has been found to make plants which express this enzyme resistant to multiple types of herbicides, has been cloned into a variety of plants (see, e.g., Hattori, J., et al. (1995) *Mol. Gen. Genet.* 246(4):419). Other genes that confer tolerance to herbicides include: a gene encoding a chimeric protein of rat cytochrome P4507A1 and yeast NADPH-cytochrome P450 oxidoreductase (Shiota, et al. (1994) *Plant Physiol.* 106(1)17, genes for glutathione reductase and superoxide dismutase (Aono, et al. (1995) *Plant Cell Physiol.* 36(8):1687, and genes for various phosphotransferases (Datta, et al. (1992) *Plant Mol. Biol.* 20(4):619. Similarly, crop selectivity can be conferred by altering the gene coding for an herbicide target site so that the altered protein is no longer inhibited by the herbicide (Padgette, 1996). Several such crops have been engineered with specific microbial enzymes for confer selectivity to specific herbicides (Vasil, 1996). A wide variety of expression cassettes are known and available.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Computer System Elements

Software elements for manipulating strings of characters which correspond to mycotoxin detoxification nucleic acids can be used to direct synthesis of oligonucleotides relevant to shuffling of mycotoxin detoxification nucleic acids. Integrated systems comprising these and other useful features, e.g., one or more of: a digital computer with additional features such as high-throughput liquid control software, image analysis software, data interpretation software, a robotic liquid control armature for transferring solutions from a source to a destination (e.g., for manipulating selection assay solutions) operably linked to the digital computer, an input device (e.g., a computer keyboard) for entering data to the digital computer to control high throughput liquid transfer by the robotic liquid control armature an image scanner for digitizing label signals from labeled assay components, or the like are a feature of the invention.

In one aspect, the invention provides an integrated system comprising a computer or computer readable medium comprising a database having at least two artificial homologous mycotoxin detoxification nucleic acid sequence strings, and a user interface allowing a user to selectively view one or more sequence strings in the database. There are a variety of sequence database programs for aligning and manipulating sequences. In addition, standard text manipulation software such as word processing software (e.g., Microsft Word™ or Corel WordPerfect™) and database software (e.g., spreadsheet software such as Microsoft Excel™, Corel Quattro Pro™, or database programs such as Microsoft Access™ or Paradox™) can be used in conjuction with a user interface (e.g., a GUI in a standard operating system such as a Windows, Macintosh or LINUX system) to manipulate strings of characters. In addition specialized alignment programs such as BLAST can also be incorporated into the systems of the invention for alignment of mycotoxin detoxification nucleic acids (or corresponding character strings).

In addition to the integrated system elements mentioned above, the integrated system can also include an automated oligonucleotide synthesizer operably linked to the computer or computer readable medium. Typically, the synthesizer is programmed to synthesize one or more oligonucleotide comprising one or more subsequence of one or more of the at least two artificial homologous mycotoxin detoxification nucleic acids, e.g., as is useful in oligonucleotide shuffling procedures.

Modifications can be made to the method and materials as hereinbefore described without departing from the spirit or scope of the invention as claimed, and the invention can be put to a number of different uses, including:

The use of an integrated system to test monooxygenase in shuffled DNAs, including in an iterative process.

An assay, kit or system utilizing a use of any one of the selection strategies, materials, components, methods or substrates hereinbefore described. Kits will optionally additionally comprise instructions for performing methods or assays, packaging materials, one or more containers which contain assay, device or system components, or the like.

In an additional aspect, the present invention provides kits embodying the methods and apparatus herein. Kits of the invention optionally comprise one or more of the following: (1) a shuffled component as described herein; (2) instructions for practicing the methods described herein, and/or for operating the selection procedure herein; (3) one or more mycotoxin assay component; (4) a container for holding mycotoxin detoxification nucleic acids or enzymes, other nucleic acids, transgneic plants, animals, cells, or the like and, (5) packaging materials.

In a further aspect, the present invention provides for the use of any component or kit herein, for the practice of any method or assay herein, and/or for the use of any apparatus or kit to practice any assay or method herein.

Accordingly, the disclosures and descriptions herein are intended to be illustrative, but not limiting, of the scope of the invention which is set forth in the following claims. One of skill will recognize many modifications which fall within the scope of the following claims. For example, all of the methods and compositions herein may be used in different combinations to achieve results selected by one of skill. All publications and patent applications cited herein are incorporated by reference in their entirety for all purposes, as if each were specifically indicated to be incorporated by reference.

What is claimed is:

1. A method of making a nucleic acid encoding a polypeptide having mycotoxin detoxification activity, the method comprising:

recombining at least two variant forms of a nucleic acid with each other to form a plurality of sequence-shuffled polynucleotides, wherein the variant forms encode mycotoxin detoxification polypeptides having mycotoxin detoxification activity and an optimal pH or optimal pH range associated with that activity; and wherein the mycotoxin detoxification activity of said mycotoxin detoxification polypeptides is reduced at pH levels that are higher or lower than the corresponding optimal pH or optimal pH range;

transferring said plurality of sequence-shuffled polynucleotides into a plurality of host cells, wherein each sequence-shuffled polynucleotide is operably linked to a promoter as part of a recombinant expression cassette; thereby forming a library of tranformants wherein the sequence-shuffled polynucleotides are expressed;

screening said library for transformants that express a recombinant mycotoxin detoxification polypeptide having improved pH stability, wherein improved pH stability is defined as a decreased susceptibility to reduction in mycotoxin detoxification activity under conditions where the pH is higher or lower than the optimal pH or optimal pH range compared to mycotoxin detoxification polypeptides encoded by said variant forms, thereby identifying a transformant that expresses a recombinant mycotoxin detoxification polypeptide having improved pH stability; and recovering from said identified transformant a polynucleotide comprising a sequence encoding the recombinant mycotoxin detoxification polypeptide having improved pH stability.

2. A method of making a nucleic acid encoding a polypeptide having mycotoxin detoxification activity, the method comprising:

recombining at least two variant forms of a nucleic acid with each other to form a plurality of sequence-shuffled polynucleotides, wherein the variant forms encode mycotoxin detoxification polypeptides having mycotoxin detoxification activity and an optimal temperature or optimal temperature range associated with that activity; and wherein the mycotoxin detoxification activity of said mycotoxin detoxification polypeptides is reduced at temperature levels that are higher or lower than the corresponding optimal temperature or optimal temperature range;

transferring said plurality of sequence-shuffled polynucleotides into a plurality of host cells, wherein each sequence-shuffled polynucleotide is operably linked to a promoter as part of a recombinant expression cassette; thereby forming a library of tranformants wherein the sequence-shuffled polynucleotides are expressed;

screening said library for transformants that express a recombinant mycotoxin detoxification polypeptide having improved temperature stability, wherein improved temperature stability is defined as a decreased susceptibility to reduction in mycotoxin detoxification activity under conditions where the temperature is higher or lower than the optimal temperature or optimal temperature range compared to mycotoxin detoxification polypeptides encoded by said variant forms, thereby identifying a transformant that expresses a recombinant mycotoxin detoxification polypeptide having improved temperature stability; and recovering from said identified tansformant a polynucleotide comprising a sequence encoding the recombinant mycotoxin detoxification polypeptide having improved temperature stability.

3. The method of claim 1, wherein the recovered polynucleotide encodes a polypeptide that has a decreased susceptibility to reduction in mycotoxin detoxification activity under conditions where the pH is higher than the optimal pH or optimal pH range, compared to any mycotoxin detoxification polypeptides encoded by said at least two variant forms.

4. The method of claim 1, wherein the recovered polynucleotide encodes a polypeptide that has a decreased susceptibility to reduction in mycotoxin detoxification activity under conditions where the pH is lower than the optimal pH or optimal pH range, compared to any mycotoxin detoxification polypeptides encoded by said at least two variant forms.

5. The method of claim 2, wherein the recovered polynucleotide encodes a polypeptide that has a decreased susceptibility to reduction in mycotoxin detoxification activity under conditions where the temperature is higher than the optimal temperature or optimal temperature range, compared to any mycotoxin detoxification polypeptides encoded by said at least two variant forms.

6. The method of claim 2, wherein the recovered polynucleotide encodes a polypeptide that has a decreased susceptibility to reduction in mycotoxin detoxification activity under conditions where the temperature is lower than the optimal temperature or optimal temperature range, compared to any mycotoxin detoxification polypeptides encoded by said at least two variant forms.

7. The method of claim 1 or 2, wherein the mycotoxin detoxification activity is selected from: inactivation or modification of a polyketide, inactivation or modification of an aflatoxin, inactivation or modification of sterignratocystin, inactivation or modification of a trichothecene, and inactivation or modification of a fumonisin.

8. The method of claim 7, wherein the mycotoxin detoxification activity is inactivation or modification of a fumonisin.

9. The method of claim 1 or 2, wherein the selection step comprises identifying a chemical modification of one or more mycotoxin in the presence of a recombinant mycotoxin detoxification polypeptide expressed by a transformant, or by detecting cell growth or survival of a transformant when cultured in the presence of the one or more mycotoxin.

10. The method of claim 1 or 2, wherein the at least two variant forms hybridize with each other when placed in a hybridization solution comprising 50% formamide at 42° C. followed by a wash of 0.2×SSC at 65° C. for 15 minutes.

11. The method of claim 1 or 2, wherein at least one variant form encodes a polypeptide selected from: a monooxygenase, a P450, trichothecene-3-O-acetyltsferase, a 3-O-Methyltransferase, a glutathione S-transferase, an epoxide hydrolase, an isomerase, a macrolide-O-acytyltransferase, a 3-O-acytyltransferase, and a cis-diol producing monooxygenase which is specific for furan.

12. The method of claim 1 or 2, wherein the polynucleotide encoding the recombinant mycotoxin detoxification polypeptide recovered from said selected transformant is cloned into an expression vector.

13. The method of claim 1 or 2, wherein said recombination step comprises in vivo shuffling of said at least two variant forms.

14. The method of claim 1 or 2, wherein the host cells are selected from the group consisting of plants, yeast, bacteria or fungi.

15. The method of claim 1, wherein the method further comprises:

(a) recombining at least one recovered polynucleotide with a further variant form of said nucleic acid to form a second plurality of sequence-shuffled polynucleotides, wherein said further variant form is the same or different from the at least two variant forms;

(b) transferring said second plurality of sequence-shuffled polynucleotides into a plurality of host cells, wherein each sequence-shuffled polynucleotide is operably linked to a promoter as part of a recombinant expression cassette; thereby forming a second library of transformants wherein the sequence-shuffled polynucleotides are expressed;

(c) screening said library for transformants that express a recombinant mycotoxin detoxification polypeptide having improved pH stability, wherein improved pH stability is defined as a decreased susceptibility to reduction in mycotoxin detoxification activity under conditions where the pH is higher or lower than the optimal pH or optimal pH range, compared to any mycotoxin detoxification polypeptides encoded by said recovered polynucleotide and said further variant form, thereby identifying a tansformant that expresses a recombinant mycotoxin detoxification polypeptide having improved pH stability;

(d) recovering from said identified transformant a polynucleotide comprising a sequence encoding the recombinant mycotoxin detoxification polypeptide having improved pH stability, and, optionally, (e) repeating (a) through (d).

16. The method of claim 2, wherein the method further comprises:

(a) recombining at least one recovered polynucleotide with a further variant form of said nucleic acid to form a second plurality of sequence-shuffled polynucleotides, wherein said further variant form is the same or different from the at least two variant forms;

(b) transferring said second plurality of sequence-shuffled polynucleotides into a plurality of host cells, wherein each sequence-shuffled polynucleotide is operably linked to a promoter as part of a recombinant expression cassette; thereby forming a second library of transformants wherein the sequence-shuffled polynucleotides are expressed;

(c) screening said library for transformants that express a recombinant mycotoxin detoxification polypeptide having improved temperature stability, wherein improved temperature stability is defined as a decreased susceptibility to reduction in mycotoxin detoxification activity under conditions where the temperature is higher or lower than the optimal temperature or optimal temperature range, compared to any mycotoxin detoxification polypeptides encoded by said recovered polynucleotide and said further variant form, thereby identifying a transformant that expresses a recombinant mycotoxin detoxification polypeptide having improved temperature stability;

(d) recovering from said identified transformant a polynucleotide comprising a sequence encoding the recombinant mycotoxin detoxification polypeptide having improved temperature stability; and, optionally, (e) repeating (a) through (d).

17. The method of claim 1 or 2, wherein said screening step comprises screening pools of transformants, wherein each of said pools comprises multiple members of said library of transformants.

18. The method of claim 1 or 2, further comprising transforming the recovered polynucleotide into a prokaryote or eukaryote.

19. The method of claim 18, wherein the recovered polynucleotide is transformed into a plant.

20. The method of claim 1 or 2, wherein recombining the at least two variant forms is performed by family gene shuffling.

21. The method of claim 1 or 2, wherein recombining the at least two variant forms comprises individual gene shuffling.

* * * * *